US012379383B2

(12) United States Patent
Regnier et al.

(10) Patent No.: US 12,379,383 B2
(45) Date of Patent: Aug. 5, 2025

(54) PROTEOFORM SPECIFIC PROCESS VALIDATION

(71) Applicant: Novilytic, LLC, West Lafayette, IN (US)

(72) Inventors: Fred Regnier, West Lafayette, IN (US); Jinhee Kim, West Lafayette, IN (US); Meena Narsimhan, West Lafayette, IN (US); Paul Dreier, West Lafayette, IN (US)

(73) Assignee: Novilytic, LLC, West Lafayette, IN (US)

( * ) Notice: Subject to any disclaimer, the term of this patent is extended or adjusted under 35 U.S.C. 154(b) by 982 days.

(21) Appl. No.: 17/476,810

(22) Filed: Sep. 16, 2021

(65) Prior Publication Data

US 2022/0137063 A1    May 5, 2022

Related U.S. Application Data

(60) Provisional application No. 63/079,244, filed on Sep. 16, 2020.

(51) Int. Cl.
*G01N 33/68* (2006.01)
*G01N 21/64* (2006.01)
(Continued)

(52) U.S. Cl.
CPC ..... *G01N 33/6848* (2013.01); *G01N 21/6428* (2013.01); *G01N 30/14* (2013.01);
(Continued)

(58) Field of Classification Search
None
See application file for complete search history.

(56) References Cited

U.S. PATENT DOCUMENTS

2018/0169657 A1    6/2018    Kelly et al.
2018/0301326 A1    10/2018   Bern
(Continued)

FOREIGN PATENT DOCUMENTS

JP    S4823917 B1    7/1973
WO    2014121031 A1  8/2014
WO    2020167852 A1  8/2020

OTHER PUBLICATIONS

Zhang, Y. et al. Integrated top-down and bottom-up proteomics mass spectrometry for the characterization of endogenous ribosomal protein heterogeneity, Journal of Pharmaceutical Analysis 13 (2023) 63-72 (Year: 2022).*

(Continued)

*Primary Examiner* — Xiaoyun R Xu
(74) *Attorney, Agent, or Firm* — Maginot, Moore & Beck LLP

(57) ABSTRACT

A system and method is provided for validating the manufacturing process for the production of complex biological compositions, and particularly for providing process validation information for evaluation by a federal regulatory agency. The system and method continuously and chronologically assess the concentration of proteoforms within the biological composition as it is being produced in a fermentor. Samples from the fermentor are analyzed in a preselected array of analysis columns, with data generated by the columns being accumulated and evaluated, and particularly compared with data from previous stages in the production process. A continuous process validation system includes top-down and bottom-up analysis sectors, each including a plurality of different analysis columns that can be selected by the controller for a particular biological composition and a particular production process.

47 Claims, 7 Drawing Sheets

(51) Int. Cl.
  *G01N 30/14* (2006.01)
  *G01N 30/72* (2006.01)
  *G01N 30/02* (2006.01)

(52) U.S. Cl.
  CPC ......... *G01N 30/72* (2013.01); *G01N 33/6845* (2013.01); *G01N 2021/6432* (2013.01); *G01N 2021/6441* (2013.01); *G01N 2030/027* (2013.01); *G01N 2030/146* (2013.01); *G01N 2560/00* (2013.01)

(56) References Cited

U.S. PATENT DOCUMENTS

2018/0372720 A1 12/2018 Wildburger et al.
2019/0362952 A1 11/2019 Bern

OTHER PUBLICATIONS

Supplementary European Search Report form in corresponding EP application 21870197 completed Jan. 11, 2024. (2 pages)S.
Qiu, Ruiqing et al., "Use of Multidimensional Lectin Affinity Chromatography in Differential Glycoproteomics", Analytical Chemistry, American Chemical Society, Dept. of Chemistry, Purdue University, May 1, 2005, pp. 2802-2809, vol. 77, No. 9, XP002574381, ISSN: 0003-2700, DOI: 10.1021/AC048751X.
Fred E Regnier, "High-Performance Liquid 1-16 Chromatography of Biopolymers", A Science, Oct. 21, 1983, pp. 245-252, vol. 222, No. 4621, XP001270295.
International Search Report and Written Opinion in corresponding PCT application PCT/US2021/50616 mailed Dec. 23, 2021.

* cited by examiner

| Post-Translational Modification Reaction | Coding Method |
|---|---|
| C-terminal lysine loss | Internal std. synthesis of PTM peptide with a $^{13}C/^{15}N$ coded amino acid. |
| N-termination pyroglutamate formation | Internal std. synthesis of PTM peptide with a $^{13}C/^{15}N$ coded amino acid. |
| Asparagine deamidation | Internal std. synthesis of PTM peptide with a $^{13}C/^{15}N$ coded amino acid. |
| Met oxidation | Internal std. synthesis of PTM bearing peptide with a $^{13}C/^{15}N$ coded amino acid. |
| Trp oxidation | Synthesis of native peptide with a $^{13}C/^{15}N$ coded amino acid. |
| Trp dioxidation | |
| His oxidation | Internal std. synthesis of PTM peptide with a $^{13}C/^{15}N$ coded amino acid. |
| Cysteine bearing peptides | $^{13}C/^{15}N$ coded cysteine bearing peptides were sythesized with a free -SH and used to synthesis of all sulfur containing variants. |

FIG. 6  PTM bearing peptides synthesized in vitro were prepared using $^{13}C$ and $^{15}N$ labeled amino acids as seen in TABLE 2.

Glycated and glycosylated peptide derivatization.

PROTEOFORM SPECIFIC PROCESS VALIDATION

STATEMENT REGARDING FEDERALLY SPONSORED RESEARCH

The present invention was made with government support under Grant No. 1R43GM97798-1, awarded by the National Institutes of Health (NIH). The government has certain rights in the invention.

PRIORITY CLAIM

This application is a utility filing from U.S. Provisional Application No. 63/079,244, filed on Sep. 16, 2020, the entire disclosure of which is incorporated herein by reference.

BACKGROUND

Cell extracts and body fluids can contain tens of thousands to a million or more proteins. Identification of these proteins depends heavily on the use of mass spectrometry (MS) and DNA databases to predict protein sequences. Samples of this complexity require liquid chromatographic (LC) or capillary electrophoretic (CE) separation before MS. It is known that with LC-MS or CE-MS, discrimination between proteins often begins with dividing samples into a hundred or more fractions based on their structural properties before MS. The MS then further fractionates the sample based on analyte mass. Analysis of intact proteins by MS is generally referred to as top-down proteomics. (See, Catherman A D, Skinner O S, Kelleher N L. *Top down proteomics: facts and perspectives*. Biochemical and Biophysical Research Communications, 2014, 445(4): 683-693.) Still another level of discrimination is achieved in the MS by fragmentation of molecular ions and separation of the resulting unique fragment ions according to their mass. These peptide-based analyses are referred to as bottom-up proteomics. (See, Angel, T. E.; Arial, U. K.; Hengelo, S. M.; Baker, E. S.; Kelly, R. T.; Robinson, E. W.; Smith, R. D. *Mass spectrometry-based proteomics: existing capabilities and future directions*. Chem. Soc. Rev. (2012), 41 (10): 3912-28).

At the cellular level, it is known that proteoform biosynthesis begins at DNA transcription with the formation of pre- and primary-mRNA species involving a combination of epigenetic imprinting, intron excision, exon rearrangement and/or shuffling, exon fusion, and RNA copy number regulation in vivo, as reflected in the chart of FIG. 2. This is followed by post-transcriptional processing in the in vivo compartment wherein mature mRNA species are produced having variations in splicing, enzymatic editing, and reading frame shift. Five or more mRNA species on average can arise from a single protein-coding gene during the course of these processing steps. Alternative splicing of mRNA, single amino acid polymorphism (SAPs) and a large number of in vivo post-translational modifications (PTMs) play an additional role in proteoform formation. Missing from this is additional layers of complexity arising from interactions between the genome, epigenome, transcriptome, proteome, and metabolome of host-cells along with environmental effects and process systems biology.

The final step in the creation of a proteoform family is in vitro post-translational modification (PTM). With in vitro PTMs, proteins can be modified by enzymes excreted into the growth medium in addition to enzymes and non-enzymatic reactions in the growth medium itself (FIG. 2). Expression of a proteoform family and the ratio of proteoforms therein is dynamic. Of particular significance is the impact of environmental variables on protein expression. (See, Li, W.; Kerwin, J. L.; Schiel, J.; Formolo, T.; Davis, D.; Mahan, A.; Benchaar, S. A. Structural elucidation of post-translational modifications in monoclonal antibodies. See, ACS Symp. Series (2015), 1201, 119-183; Gault, J.; Malosse, C.; Machata, S.; Millien, C.; Podglajen, I.; Ploy, M.-C.; Costello, C. E.; Dumenil, G.; Chamot-Rooke, J., Complete posttranslational modification mapping of pathogenic *Neisseria meningitidis* pilins requires top-down mass spectrometry. Proteomics (2014), 14, (10), 1141-1151)). The transition from exponential to the stationary phase of growth is another variable. (See, Sandalio, L. M.; Gotor, C.; Romero, L. C.; Romero-Puertas, M. C. Multilevel regulation of peroxisomal proteome by post-translational modifications. Intern. J. Mol. Sciences (2019), 20(19), 4881).

This goes to the heart of monitoring process continuity in proteoform biosynthesis. Beyond the fact that PTM bearing mAb variants can vary in biological activity, some PTMs convey toxicity or immunogenicity. With mAbs, the most common of these in vitro PTMs are pyroglutamic acid formation at protein N-termini, degradation at N- and C-termini, conformational changes involving sulfhydryl and disulfide bridge scrambling, deamidation, methionine oxidation, glycation, and glycosylation variants; some of which are critical quality attributes (CQAs) of an mAb. Many of these isoforms are unnatural and vary substantially in magnitude, biological activity, immunogenicity, and propensity to aggregate. Through all of these steps, a monoclonal antibody family has approximately 130 glycoforms and a series of other post-translational modifications (PTMs) distributed across a single family.

Process monitoring by these methods uses proteoform structures as diagnostics, but in a way that is different than other diagnostic modes. In health/disease diagnostics, biomarkers are used to assess the biological state of a cell or organism, but only after searching an entire proteome for proteins associated with the biological phenomenon in question and confirming that association with thousands of patients. The FDA requires tight levels of validation before accepting clinical diagnostic methods based on biomarkers.

Process diagnostics is the opposite. The exact biological state of the host-cells when a sample is taken for analysis is unknown. Moreover, that biological state can generally not be replicated, as is possible in disease state and normal cells. Use of genetically engineered host-cells to produce a proteome family of a fixed concentration ratio is not under tight cellular control. That is why environmental variables have such a large impact on proteoform and CQA ratios. Systems biology has not evolved to the level that tight regulatory control of proteoform and CQA ratios are possible.

Diagnostics require a point, or points, of reference to what is considered a normal continuum or gradual evolution to a new biological state. Cell aging would be such an evolution to a new state. In a fermentor five points of reference are available:
  (i) the proteoform/CQA ratio at a particular time point just before a sample was taken;
  (ii) the proteoform/CQA ratio from an identical prior production run at the same elapsed time;
  (iii) metabolite and nutrient ratios at the same points in time;
  (iv) accompanying host-cell protein ratios at the same time; and
  (v) environmental sensor data taken at the same relative time.

SUMMARY OF THE DISCLOSURE

Referring to the flowchart of FIG. 1, process monitoring problems in proteoform processing are addressed by identifying potential problems as they occur (Segment A), selecting and prioritizing confirmation methods Segment B, confirming that the problem exists in Segment C, and then implementing a solution in Segment D. Samples are withdrawn from the fermentor on an hourly basis. Intact therapeutic proteins are analyzed chromatographically or electrophoretically in a first sector of the instrumentation of the analytical system by preselected, invariant analytical strategies. Data from these analyses are digitized and compared by the data system to prior reference points in Segment A. Apparent changes in relative concentration of proteoforms, metabolites, nutrients, host-cell proteins, and environmental sensors are determined by the data system based on prior reference data. Apparent deviations from these reference points trigger the data system to search for the most appropriate confirmation methods in Segment B and to initiate the selected methods in a second sector of the instrumentation (Segment C). The object of the steps in Segment C are to: (i) identify the probable proteoform(s) contributing to the changes based on separation properties; and (ii) predict trypsin digest peptide fragments from these proteoforms that would verify identification of the proteoform(s). At a methods level this requires the data system in Segment B to: (i) select and sequentially apply a series of methods that will affinity select the relevant proteoform(s); ii) select methods leading to enzymatic digestion of the proteoforms and identify signature peptides; (iii) execute MRM based quantification of the predicted peptide fragments; and (iv) identify CID induced fragment ions of the predicted peptide(s) to be fragments by LC-MS. Confirmation of the problem is achieved by further data analysis in Segment D.

Host-cell protein (HCP) concentration and constituent ratios are examined using chromatographic or electrophoretic modes after therapeutic protein removal by affinity. HCP is obtained by transferring apparently variant fractions from a top-down sector of the instrumentation into the second sector for peptide analysis in the same manner as that used with therapeutic proteins. Apparent concentration and ratio changes in the first analytical sector are extracted from the analytical data and noted. Further structural identification of the HCP is obtained by transferring apparently variant fractions from the top-down sector to the second sector for peptide analysis.

Exo-metabolites and nutrients are analyzed by first removing components greater than a thousand Daltons by sized exclusion chromatography. HCPs can also be removed with a down-stream HPC targeting affinity column. Absorbance before and after HPC removal gives a rough estimate of HCP concentration. Again, apparent concentration and ratio changes in the first analytical sector are extracted from the analytical data and noted. The metabolite and nutrient fraction are then transferred to a chromatography column where they are adsorbed at the column inlet and inorganic salts are allowed to pass to waste. Identifications are achieved by liquid chromatography-mass spectrometry (LC-MS). The dynamics of these substances reflect nutrient consumption by host-cells, excretion, and cell death.

DESCRIPTION OF THE FIGURES

FIG. 6 are chemical diagrams showing synthesized PTM-bearing peptides.

DETAILED DESCRIPTION

Figure 1:
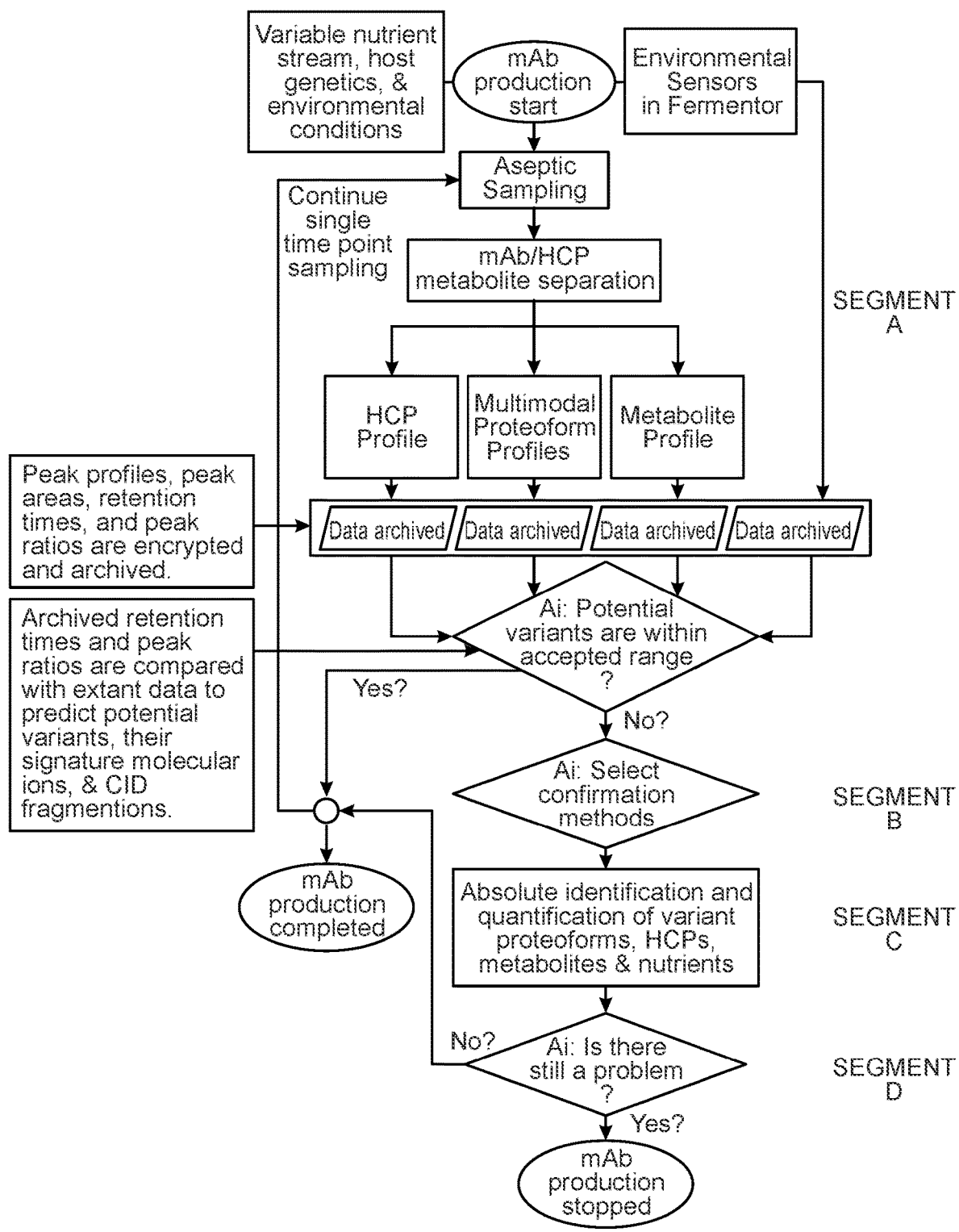
FIG. 1 is a flowchart of steps in a method for proteoform specific process validation according to the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Preferred embodiments of the invention are directed at identifying and quantitatively evaluating deviations in proteoform/CQA ratios relative to reference points through the series of steps in the flowchart of FIG. 1. Specifically, as will be appreciated by one skilled in the art, various iterations and embodiments of the methods and possible analyses are described below. However, the invention is not limited to these iterations or embodiments, or to the specific order of steps presented herein. Variations in the number and order of steps, addition of other steps, and combinations of aspects of the various embodiments herein, all fall within the scope of the claimed invention. For example, and by way of illustration, although the embodiments disclosed herein discuss different aspects of the separation, detection, identification and quantification of proteoforms/CQAs, host-cell proteins, metabolites, and nutrients, these steps can be performed in various orders, in multiple combinations and at various times as directed by the system analytics, depending on the quality and character of the sample derived from the fermentor.

Figure 3:
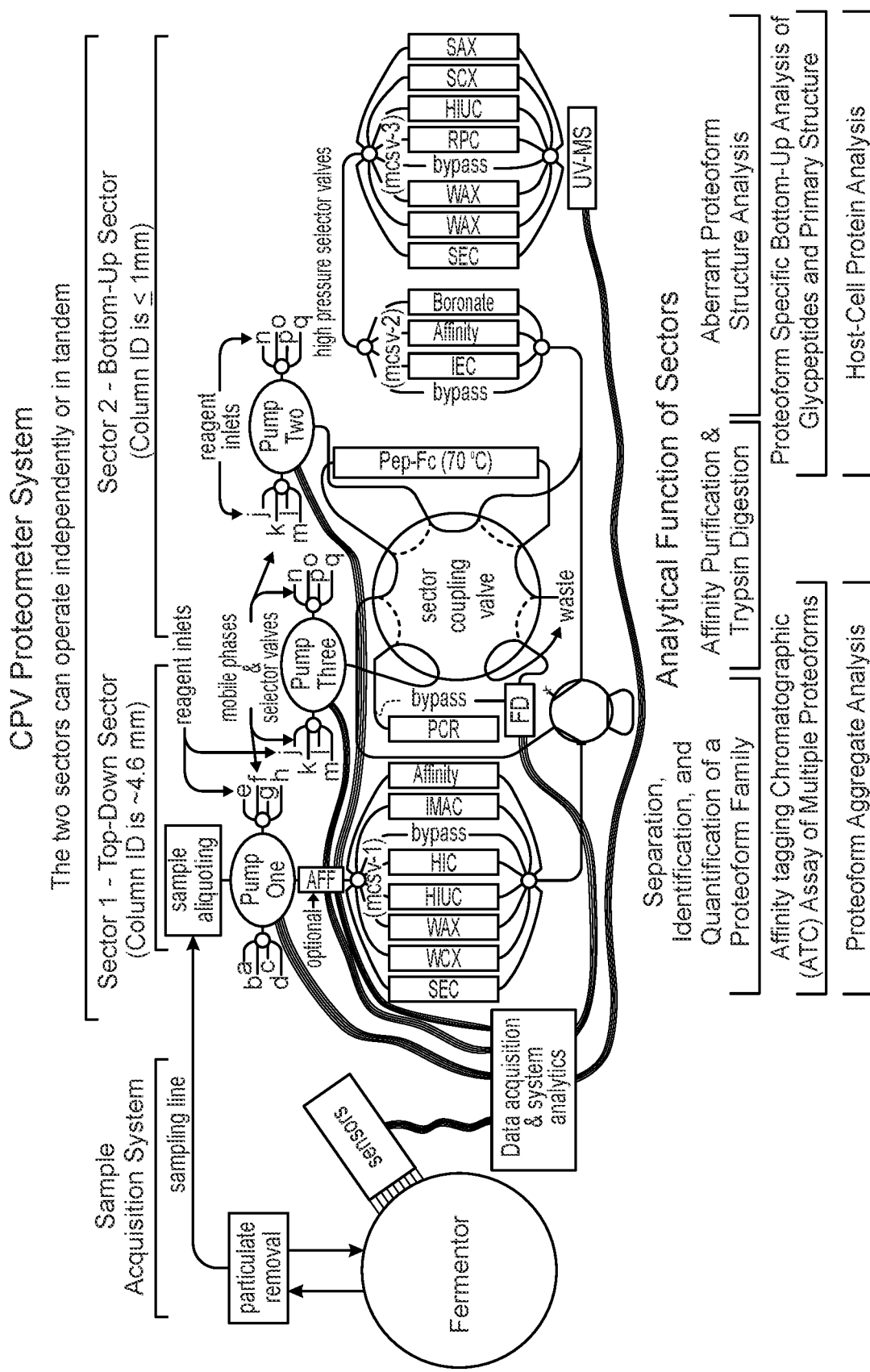
FIG. 3 is an annotated diagram of a continuous process validation system according to the present disclosure.
Figure 4:
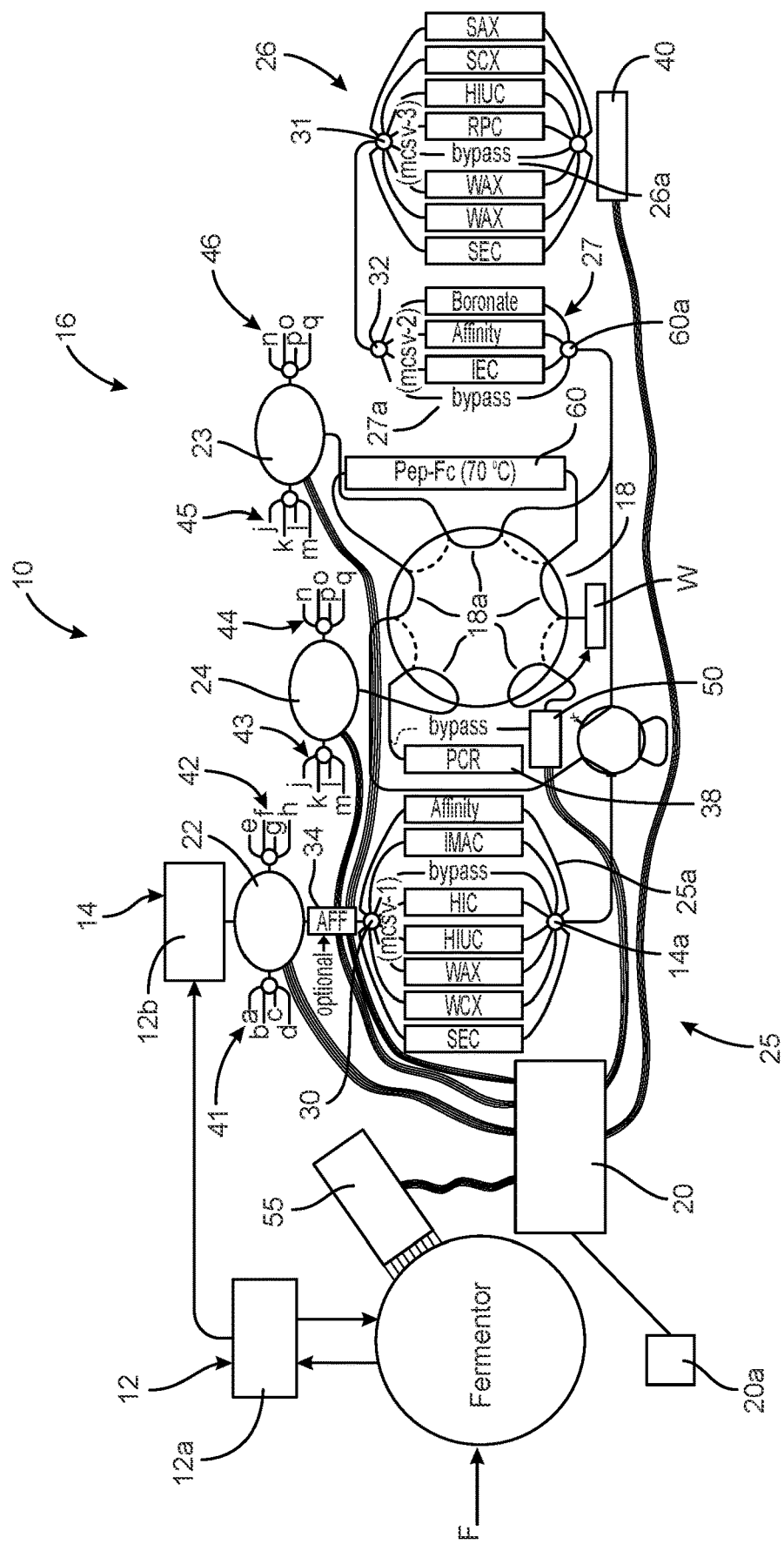
FIG. 4 is a diagram of the continuous process validation system according to the present disclosure.

The present disclosure contemplates a continuous process validation system to implement the method steps of FIG. 1. The process validation system 10, shown in FIGS. 3-4, includes two sectors 14, 16 that process samples obtained from a fermentor F by a sampling system 12. The fermentor F can be of conventional design for proteoform biosynthesis. The sampling system 12 can be of conventional design configured to extract samples from the fermentor, including a particulate removal component 12a and a sample aliquoting component 12b. The sectors of the process validation system 10 include a top-down sector 14 and a bottom-up sector 16. By way of illustration, FIGS. 3-4 shows that an intact protein sample from a fermentor can be resolved in seven ways within the top-down sector 12, as described in more detail herein. Within these modes, protein resolution can be achieved on the basis of charge, hydrophobicity, hydrophilicity, affinity for an immobilized lectin, histidine content, affinity for an antibody, molecular size, or any combination thereof. The CPV system 10 includes a sector coupling valve 18 that can couple the output 14a to the input 16a of the bottom-up sector 16. With this ability to convey the sample aliquot among sectors and bypasses within the sectors of the process validation system, analytes resolved with a particular separation mode can be detected by absorbance using a uv-vis/diode array detector 40, fluorescence by a fluorescence detector 50, or mass analysis by mass spectrometer 40. In addition, analytes tentatively identified in top-down sector 14 as varying in concentration can be confirmed in the bottom-up sector 16 through the use of methods selected by system analytics implemented by a controller 20. As in the top-down sector 14, multiple separation modes and combinations thereof can be used in bottom-up sector 16 to resolve peptides derived from proteins and proteoforms. In total, the two sectors 14, 16 provide over 500 method combinations using the multimodal four-dimensional analytical strategies described herein.

Terms used herein have meaning as commonly understood by one of ordinary skill in the art. While the terms herein are used to describe particular embodiments and versions of the present invention, they are not intended to limit the scope of the invention except as specifically stated in the claims.

An "analyte" according to versions of the present invention refers to a proteoform, host-cell protein, metabolite, or nutrient in a sample for which a measurement is desired. "Analytes of interest" refer to proteins, CQAs, metabolites, or nutrient of which changes in their concentration could impact therapeutic protein quality without regard to whether they are known to exist in a sample.

Figure 2:
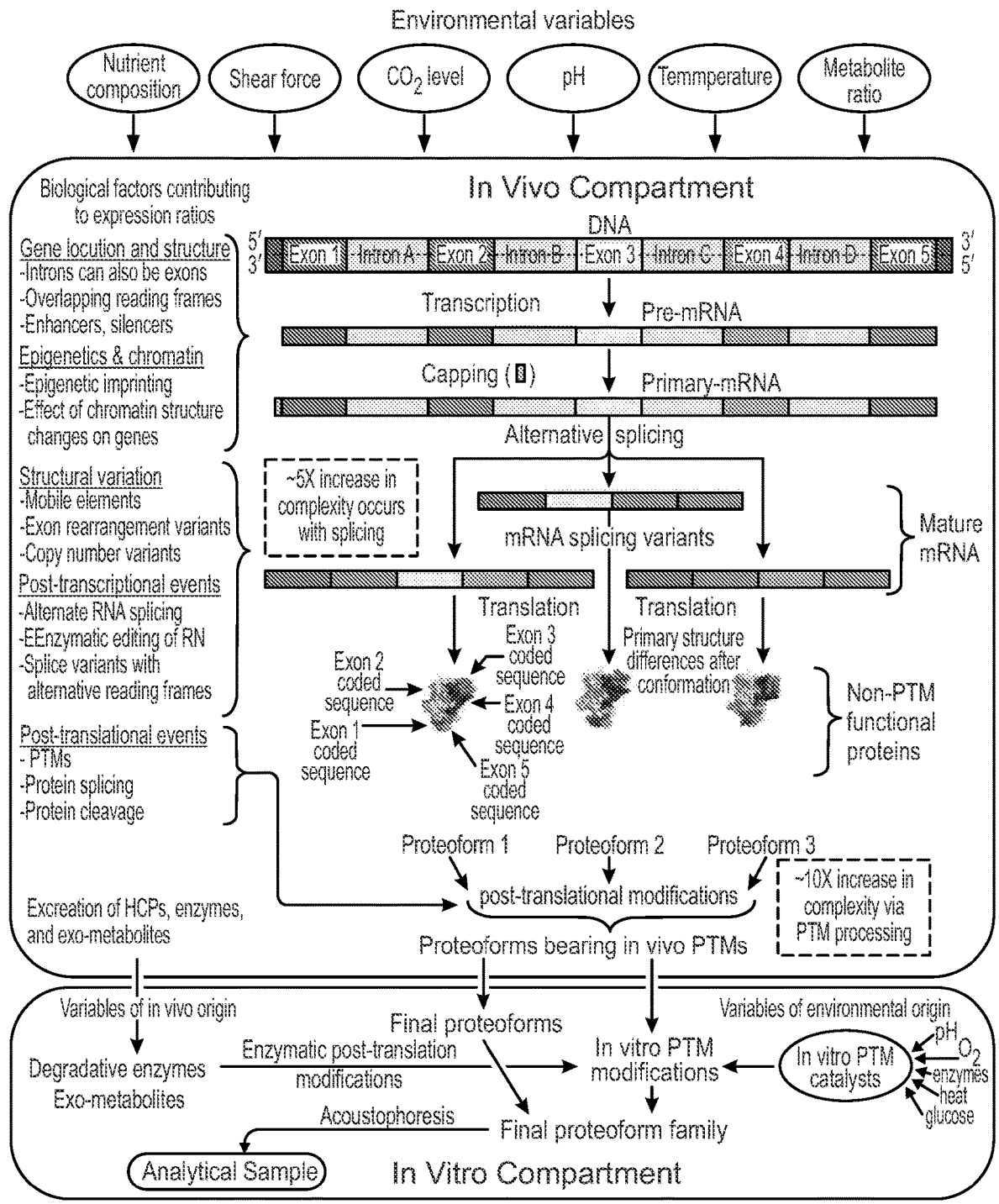
FIG. 2 is a chart describing proteoform synthesis in a fermentor.

As known to those skilled in the art, a monoclonal antibody (mAb) is generally made up of multiple, structurally related protein isoforms. The terms "mAb analyte" and "mAb expression" refer to a mAb family of structurally related isoforms referred to as proteoforms or CQAs that are coded by the cellular genome of host-cells and the environment in a fermentor. As seen in FIG. 2, it is understood that through multiple levels of DNA transcription pre- and primary-mRNA species are formed in cell nuclei as a result of epigenetic imprinting, intron excision, exon rearrangement, exon fusion, and RNA copy number regulation along with post-transcriptional processing and post-translational modifications; the net result being a proteoform family bearing multiple identical structural elements but differing at specific structural sites.

"Analyzing" as described herein refers to the application of appropriate techniques in the top-down sector 14 or selected by system analytics in the bottom-up sector 16 that determine one or more analytes of interest using quantitative analytical techniques that measure the concentration of one or more analytes of interest through the use of absorbance, fluorescence, or mass spectral detection methods A "sample" refers to an aliquot of fermentation medium obtained from the fermentor F containing analytes of interest drawn from a fermentor during process development or a production campaign.

"Purifying" a sample according to versions of the present invention refers to at least partially separating analytes of interest, if any, from the remaining components of a sample without substantially altering the properties of the analyte of interest. Purification or purifying refers to a procedure that enriches the amount of analytes of interest, if any, relative to other components in the sample that might interfere with optical detection or mass spectrometric analysis of the analytes of interest. This relative reduction does not require that substance interfering with the analysis be substantially or entirely removed.

"Lower limit of quantification" as used herein refers to the lowest point at which analyte produces sufficient signal in a detector to identifiable, discrete, and reproducible with a relative standard deviation of less than 20% and accuracy of greater than 80%. The "limit of detection" is the point at which the value measured using optical detection or mass spectrometry is equal to or less than the uncertainty associated with that value, and is defined as three times the relative standard deviation of the mean at zero concentration.

As accepted in the field of proteomics, the term "top-down" refers in the present disclosure to methods of protein and protein isoform identification and quantification using intact proteins. "Bottom-up" refers to methods used in the identification, characterization, and quantification of proteins and proteoforms of peptides derived from proteolytic digests thereof.

The term "process validation system" refers in the present disclosure to an instrument platform designed to execute top-down and bottom-up identification, characterization, and quantification of proteins and proteoforms, as depicted by the system 10 shown in FIGS. 3-4. Distinguishing features of this instrument system are that: (i) cell free analytical samples are automatically withdrawn from a fermentor by the sampling system 12 at fixed time intervals throughout a production campaign; (ii) top-down (TD) and bottom-up (BU) analyses are automatically executed in separate sectors within the platform; (iii) detection by the columns in the column array 25 of the TD sector 14 is based on molecular recognition and is proteoform specific; (iv) methods and the sequence in which they are applied in the BU sector 16 are determined by artificial intelligence (AI); (v) detection and quantification of signature peptides by the columns in the column arrays 26, 27 of the BU sector 16 is based on isotope ratio analysis by mass spectrometry; (vi) the TD and BU sectors 14, 16 can operate in parallel or in tandem; (vii) analytes can be transferred between the sectors to construct multi-step methods; (viii) multiple modes of analysis are executed in each sector; (ix) analytical modes, and the sequence in which they are applied in each sector, are variable, and are selected to ensure assessing process continuity; (x) analytical method selection and sequencing is controlled by artificial intelligence; (xi) analytical data is rendered immutable during acquisition, and xii) the system can operate in a manufacturing environment. When used in continuous up-stream process monitoring the platform is referred to herein as a "continuous process validation" system (CPV system).

The sampling system 12 can be configured to extract samples directly from the fermentor by acoustophoresis, membrane filtration, or a combination thereof. A particle free aliquot is transported from the fermentor to a sample inlet of the CPV system by a low-pressure pump 22. Beyond removing particulates and cellular debris, no molecular level fractionation occurs in the sampling system 12. The sample(s) is directed through analysis column arrays 25, 26, 27. The column array 25 of the TD sector include affinity, IMAC (immobilized metal affinity chromatography), HIC (hydrophobic interaction chromatography), HILIC (hydrophilic interaction chromatography), WAX and WCX (weak anion and cation exchange) and SEC (size exclusion) columns, as are well known in the art. In a specific embodiment, the columns of the TD column array 25 have an inner diameter of about 4.6 mm or in some cases about 7.8 mm. The column array 26 of the BU sector 16 includes SAX and SCX (strong anion and cation exchange), HILIC, RPC (reversed-phase chromatography), WAX and SEC columns, also as known in the art. The column array 27 of the BU sector includes Boronate affinity, affinity (with selected affinity media) and IEC (ion exchange) columns, as known in the art. In a specific embodiment, the columns of the TD column array 25 have an inner diameter of less than about 1 mm. Each set of columns includes a respective bypass 25a, 26a, 27a that can be accessed to bypass the analysis columns. Mcsv (multi-channel selection valve) valves 30-32 direct the sample to the appropriate columns or bypass within the column arrays 25-27. It is understood that each of the columns in the arrays 25-27 is configured for a specific type of analysis of the sample aliquot. Mcvs pump 22 pumps the sample aliquot through the TD sector 14, while a mcsv pump 23 draws the sample through the columns 26, 27 of the BU sector 16. A third mcsv pump 24 can pump a sample through a PCR (post column reactor) column 38 for detection of certain genetic material.

In general terms, the CPV system 10 shown in FIGS. 3-4 is coupled to an existing fermentor F that is constantly monitored by environmental sensors 55. Data from the sensors is provided to a controller 20 that is configured to execute software to evaluate the sensor data, and in particular to determine landmarks in the process occurring in the fermentor. When predetermined environmental conditions arise within the fermentor F, the controller 20 directs the sampling system 12 to extract a sample from the fermentor. The controller 20 then operates the two sectors based on a particular validation protocol to determine the integrity of the sample, and thus the validity of the process occurring in the fermentor. The controller 20 thus activates at least pump 22 to direct the sample to the TD sector 14. Depending on the validation protocol, the controller may direct the injection of particular reagent(s) into the sample through a corresponding one of the ports 41, 42 prior to passage of the sample into one of the analysis columns in the column array 25 (26 or 27). The controller then actuates the mcsv valve 30 to direct the sample to a selected one of the analysis columns of array 25, again according to the pre-determined validation protocol. In some cases, the controller directs the sample to the bypass 25a so that the sample can move from the outlet 14a of the TD sector to the BU sector 16. In other cases, the sample has passed through one of the analysis columns and is then to be directed from the outlet 14a to the BU sector 16.

For a sample directed to the BU sector, the controller orients the sector coupling valve 18 so that one of the internal branch loops 18a places the pump 23 in communication between the outlet 14a of the TD sector and the inlet 16a of the BU sector. The controller can also direct reagents to be introduced into the sample at a corresponding one of the ports 45-46. In the BU sector 16, the controller 20 can activate the mcsv valves 31, 32 to direct the sample to the appropriate one of the columns in the column arrays 26, 27.

Prior to exiting the BU sector 16, the sample passes through a uv-vis/diode array detector and mass spectrometer 40. In some protocols, prior to entering the BU sector, the sample is directed through a Pep-Fc proteolysis column 60 by the sector coupling valve 18 in which an unfractionated proteoform family that has been affinity selected can be digested before analysis of the resulting peptide classes in the BU sector columns, wherein the affinity column of the column array 27 is resistant to trypsin digestion.

In other validation protocols, the sample does not need to pass through the BU sector 16, so the sector coupling valve 18 can be oriented by the controller to direct the sample to waste W or to the PCR column 38, or alternatively through a bypass, powered by the mcsv pump 24, for subsequent evaluation by a fluorescence detector 50. Reagents can be introduced to the sample at the mcsv pump 24 through ports 43-44.

As described in more detail herein, the operation of the CPV system 10 is managed by the controller 20 according to predetermined validation protocols. In addition to the predetermined steps of the protocols, the controller monitors the data generated by each of the analysis columns of the arrays 25-27. The determination whether a particular sample is directed to the BU sector 16 can be based on the results of the analysis in the TD sector 14, so the controller evaluates the TD sector data to make that determination. The controller is thus configured to make on-the-fly decisions as needed to manage the validation process. Other details of the CPV system 10 and controller 20 are described below with specific examples.

The analysis columns identified in the specific embodiment of FIGS. 3-4 are selected for monoclonal antibody analysis. A preferred embodiment of the CPV system for monoclonal antibody (mAb) analysis uses column switching among the columns in column array 25 in sector 14, by way of mcsv valve 30, and the columns of arrays 26, 27 in sector 16, by way of mcsv valves 31, 32, respectively, to enable rapid, automated, sequential switching from one chromatographic or electrophoretic mode to another within a 30-60 min time frame during continuous process validation, as determined by the controller 20. Relative retention of proteoforms varies between separation modes in a structure specific manner controlled by a controller 20 using artificial intelligence (AI). Although the preferred modes may vary between proteoform families, ion exchange, hydrophobic interaction, immobilized metal affinity, and hydrophilic interaction chromatography are preferred for the separation of intact proteins, although electrophoretic modes of separation can be suitable as well. Analytes eluting in each separation mode are identified, quantified, plotted as a concentration ratio and the plots compared with earlier analyses in the production run and equivalent fermentation times from accepted standard samples in a data acquisition component of the controller 20. A user interface 20a is connected to the controller and can include a display for displaying data generated by the controller, as described herein. The function of multimodal analysis is to validate in multiple modes of analysis the degree of continuity in a manufacturing process.

One of the columns of array 25 of the TD sector 14 implements size exclusion chromatography (SEC) or capillary electrophoresis for mAb proteoform aggregate analysis. In one embodiment, a conventional electrophoresis module can be connected to bypass 25a. Environmental conditions in a fermentor can vary sufficiently to cause immunogenic aggregates of mAbs to form, diminishing product quality. SEC and gel electrophoresis are capable of detecting mAb aggregates containing up to four proteoforms. Effluent from the SEC column bearing metabolites and nutrients is directed to the column arrays in BU sector 16 for separation and quantification, as reflected in Segment A of the flowchart in FIG. 1.

In a preferred embodiment, artificial intelligent (AI) is implemented by the controller 20 in the analysis of data generated in the TD sector 14 to sense potential variations in the manufacturing process and to select peptides for analysis in the BU sector 16. This approach provides independent validation of structural variations. Modes of analyses in the BU sector 16 are directed by AI (Segment B of FIG. 1).

A preferred mode of operation in the TD sector 14 of the CPV system is to structure specifically detected intact proteoforms with high sensitivity as they elect from columns by non-covalently tagging analytes with a fluorescent labeling reagent, introduced through one of the ports 41, 42. Analyte tagging agents (ATAs) as described herein uniquely bind to a specific structural motif within all members of a proteoform family by molecular recognition. More specifically molecular recognition is an interaction between an analyte and an ATA which exhibits molecular complementarity to the analyte through non-covalent bonding; hydrogen bonding, metal coordination, hydrophobic forces, van der Waals forces, π-π interactions, and/or electrostatic effects being examples. A further preferred embodiment is that molecular recognition ATAs are of low molecular weight to enable binding in a small space within a protein; peptides, aptamers, and affimer being the preferred targeting reagents. As appreciated by one skilled in the art, a fluorophore may be a structural component of an ATA; enabling fluorescence detection in multiple ways. A preferred embodiment with the CPV system is by Förster resonance energy transfer (FRET) wherein a donor fluorophore bound by molecular recognition at a specific site on the surface of an analyte is excited and emits fluorescent energy that excites an adjacent acceptor fluorophore in an ATA similarly bound by molecular recognition on the analyte surface.

The BU sector 16 of the CPV system is configured to achieve identification and quantification through the addition of isotopically labeled internal standards to proteolytic digests that are than analyzed by liquid chromatography-mass spectrometry (LC-MS). The internal standard is a mixture of all possible signature peptides that is added in a known amount prior to analysis of a sample, wherein the internal standard is generated by synthesis of peptides bearing $^{13}C$ labeled amino acids or by primary amine labeling with a $^{13}C$ tagged derivatizing reagent, introduced through one of the ports 45, 46. This allows for any signature peptide chosen by the system analytics for analyte identification to be in the internal standard mixture. An alternative labeling approach used with glycated proteins and glycoproteins is to acylate one or more primary amines in all peptides with a heavy isotope labeled acylating agent; $^2H_3$ acetate and $^{13}C_3$ labeled propionate being the preferred labeling agents. Monoclonal antibody proteoforms can vary substantially in amount, critical quality attributes, and therapeutic efficacy as noted above. For these reasons, quality is often referred to holistically as "high," or "moderate-to-low" based on properties of the family as a whole. Assessing process variability during a production run is most easily achieved by qualitative and quantitative profiling of a family as a function of time rather than by CQAs.

The continuous process validation (CPV) system 10 depicted in FIGS. 3-4 is a unique instrument platform that provides: i) rapid tentative identification, quantification, and concentration ratios of proteoforms in the TD sector 14 on an hourly basis; ii) AI based selection of methods and signature peptides to confirm the TD sector measurements in the BU sector 16; iii) execution of these methods in the presence of high concentrations of host-cell proteins, metabolites, and growth medium; iv) recognition and quantification of multiple PTM types within a proteoform family; v) differentiation between proteoforms arising in different cellular compartments; and vi) automatic execution of these methods at-line in a non-laboratory, up-stream processing environment on an hourly basis for two weeks.

The method and system disclosed herein can be used to monitor the production of any recombinant protein, although the instrument platform and methods it enables were specifically designed to qualitatively and quantitatively monitor products composed of multiple proteoforms.

Fermentor Sampling

The sampling system 12 and the particulate removal component 12a are configured to aseptically remove cells and debris from the soluble sample components in fermentor broth. Acoustophoresis and membrane filtration are preferred methods. With acoustophoresis a stream of broth is transported through a rectangular channel bearing a half wavelength resonator that directs an acoustic wave across the flow channel. Cells moving through the channel experience higher acoustic force than macromolecules and are caused to focus at a particular position in the flowing stream. By balancing linear velocity and acoustic power, particles were axially segregated and directed to a specific outlet while soluble analytes exit through another outlet. Cells and cellular debris were either returned to the fermentor or discarded. Among the advantages of acoustophoretic sampling are that the separation channel does not block during a production campaign, the system is small and easy to sterilize, sampling volumes are small relative to the volume of a fermentor, and acoustic focusing is sufficiently gentle that cells are not disrupted.

Membrane filtration via a hollow fiber system is a second sampling option, either by diffusive transport alone or with a tangential flow filtration (TFF) system of the type used by Repligen. With TFF, soluble proteins are extracted from the fermentor continuously. This makes sampling easy and fortuitously removes particulates. Permeate provided by a TFF system can be used for continuous process validation. Membrane porosity and pore size determine the throughput and molecular weight of analytes selected. In a specific embodiment, molecular weight cut-off of choice for monoclonal antibodies and many therapeutic proteins is 500 kilodaltons (kDa). This precludes transport of cells, cellular debris, and many viruses into permeate while still allowing mAb harvesting.

In the absence of a production scale membrane harvesting system on the fermentor, a small analytical KrosFlo® Research II System with a digital pressure monitor, a 500 kDa MCO membrane cartridge of 65 cm length, 60 cm$^2$ surface area, and 2 mL membrane cartridge volume from Spectrum (a subsidiary of Repligen) can be used in certain specific embodiments. Permeate is transported directly to the CPV system, while unused permeate is sent to waste W. The Spectrum membrane sampling system can be operated in either the dialysis or TFF mode.

In another specific embodiment, direct sampling of broth from the fermentor can be achieved aseptically with an All-Pure Technologies TAKEONE™ sampling system provided by AllPure Technologies LLC of New Oxford, PA This device is capable of simultaneously withdrawing up to nine separate streams aseptically from a fermentor. Continuous or intermittent sampling through any of these lines is possible. Bacteria, cellular particulates, and viruses were removed from crude broth samples by centrifugation. An alternative is to use this approach with tandem acoustophoresis to remove particulates.

Analysis Time-Window

An objective in the continuous process validation method disclosed herein is to gather sufficient data to estimate process variability. Sampling time is a function of the rate at which proteoform concentration can change significantly in a fermentor. This is estimated to be less than 1% per hour as shown below. The minimum top-down sampling time through the TD sector 14 can be set at 30 min., which will provide 672 samples at maximum in a two-week production run. This also happens to be the minimum time a liquid chromatography or electrophoresis system can achieve a high-resolution separation in most cases.

Quantitative Mapping of Proteoform Elution Profiles

The objective of quantification in continuous process validation is to assess changes in proteoform synthesis rate that would indicate a process deviation. As seen in FIG. 2, proteoforms can be synthesized in many ways. Moreover, proteoforms can differ in CQA content. Differential rate changes in the synthesis of proteoforms during production impact their concentration ratios and therefore the therapeutic efficacy of a proteoform family. The discussion below relates to types of measurements a CPV system must make to validate process continuity.

Changes in the rate of proteoform synthesis during fermentation are due to: i) alterations in cellular expression, in vivo post-translational modifications, and excretion into the growth medium; ii) in vitro post-translational modifications; iii) the rate of cell proliferation; iv) cellular aging; and v) cell death. The total amount ($A_{tn}$) of a proteoform $\underline{A}$ synthesized within a fermentation time-window n will be $A_{tn} = r_{sn}^a t_n + A_{on}$ where $r_{sn}^a$ is the rate of $\underline{A}$ synthesis in time-window n, $A_{on}$ is the amount of $\underline{A}$ in the fermentor at the start of n, and $t_n$ is the length of time-window. The synthesis rate per unit time $r_{sn}^a$ is a function of the slope in a concentration versus elapsed time plot. The time-window n and time $t_n$ are determined by the portion of the slope that remains constant. Additional methods of assessing process continuity are to plot either or both of proteoform ratios as a function of time, and the first derivative of time versus concentration plots.

It is realistic that proteoform rate of synthesis $r_s^a$ will change multiple time according to the equation $A_{tot} = A_{tw1} + A_{tw2} + \ldots A_{twn} = t_{w1} r_{s1}^a + t_{w2} r_{s2}^a + \ldots t_{wn} r_{sn}^a$. The term $A_{tw}$ is the amount of material produced in a specific time-window, $t_{wn}$ is the width of a time window, and $r_{sn}^a$ is the rate of synthesis of a proteoform $\underline{A}$ in the time window. Differences in the rate of synthesis will be revealed by multiple slope changes in a proteoform time versus concentration plot.

The ease with which a rate change can be detected varies with time due to the increasing amount of $A_{tot}$. At the stage where $A_{tot} = A_{tw1} + A_{tw2}$ the $A_{tw1}/A_{tot}$ or $A_{tw2}/A_{tot}$ ratios would be much larger than the $A_{tw50}/A_{tot}$ ratio in time window #50 of a two week production run. This is illustrated in the ideal case where the rate of synthesis ($r_s^a$) is constant during a production run. The amount of a proteoform produced in an hour would be $A_{hr}$ (%) = $A_{tot}/(100t)$. At the end of 4 days $A_{hr}$ (%) would equal ~1% of $A_{total}$ whereas at the end of the 14$^{th}$ day it would be 0.3%. These calculations are the basis for establishing sampling times of an hour, as discussed above, which are sufficient to detect changes in the rate of proteoform synthesis.

Sudden environmental changes that trigger the synthesis of an aberrant proteoform ($\underline{A}_{ab}$) are much easier to detect as seen in the equation $A_{tn} = r_{s1}^{ab} t_n$. There is no $A_{on}$ term. The $r_s^a/A_{on}$ problem noted above is eliminated.

Determining changes in the rate of synthesis in a continuous harvesting system is more complicated. Assuming the volume of growth medium is constant during sampling, the amount of proteoform $\underline{A}$ synthesized during a time-window of $t_n$ would be $A_{tn} = \underline{A}_{on} + r_{sn}^a t_n - r_{hn}^a t_n$ where $r_{hn}^a$ is the rate at which $\underline{A}$ is being harvested. Volume changes during harvesting would mean that $A_{on}$ is variable and could differ in each time window.

Compartmentation of Proteoform Synthesis

As is known in the art, synthesis of a proteoform family in a fermentor occurs in two compartments; in vivo and in vitro, as reflected in FIG. 2. The significance of this in process monitoring is that proteoform structural attributes derived in these compartments are different and independently regulated. Recognizing the compartment within which a deviation is occurring is an important diagnostic.

Major portions of the primary structure of a proteoform family are coded by exons common to all family members (see FIG. 2). The Fc region of a monoclonal antibody family is an example that is exploited in mAb specific detection herein. A preferred embodiment of signature peptide detection and monitoring with the CPV system is in determining the rate of synthesis and total amount of a proteoform family via bottom-up proteomics. This is achieved with mAbs by using a signature peptide from the Fc region identified during process development that is common to all proteoforms. A heavy isotope labeled version of this signature peptide was synthesized and added to an aliquot of a proteolytic digest as an internal standard ($SP_{is}$).

Isotope Labeling and Coding $^{13}C$ and $^{15}N$ labeling and coding are preferred as a means to preclude separation of the $SP_{is}$ and SP during liquid chromatographic separations. Through $^{13}C$ and $^{15}N$ mass coding, in vivo signature peptides can be recognized as doublets separated by a specific mass. The $SP_{is}$/SP isotope ratio arising from multiple reaction monitoring (MRM) is assessed via liquid chromatography/mass spectral analysis of proteolytic digests. $SP_{is}$/SP ratios are used in determining the rate of synthesis and total amount of proteoform family members in time-window aliquots. Constant $SP_{is}$/SP ratios of signature peptides throughout a production run indicate the rate of expression and post-translational modification is unchanging.

A potential problem with this approach is when another peptide in the proteolytic digest of a proteoform family has the same mass as the $SP_{is}$ or SP. When the interfering peptide has the same mass at the $SP_{is}$ it is easiest to resolve the problem by changing the mass of the $SP_{is}$ through isotope coding. When the mass of the interfering peptide is the same as the SP it is best to use a different signature peptide or collision induced fragmentation of the peptides in isotope ratio analysis.

Structural attributes common to multiple, but not all proteoforms can arise from exon deletion or scrambling (see FIG. 2) along with post-translational modifications. These in vivo derived features also have signature peptides that are quantifiable by MRM isotope ratio monitoring. Signature peptides can be uniquely coded by increasing the number of $^{13}C$ atoms in the internal standard, but the preferred mass difference between the $SP_{is}$ and SP used herein with in vivo modifications was 3 amu.

In vitro reactions involving degradation at N- and C-termini, conformational changes arising from sulfhydryl and disulfide scrambling, deamidation, methionine oxidation, and glycation occur at multiple sites. A plus four or eight $^{13}C$ labeling code is used to identify in vitro PTM bearing signature peptides. Again the $SP_{is}$/SP isotope ratio is used to determine synthesis rate changes and total concentration of aberrant proteoforms. A unique aspect of these in vitro features is that synthesis is incomplete; multiple PTMs can occur in the same proteoform and are not proteoform specific. This produces an array of variants of similar structure. A proteoform that has been deaminated for example has any one or all the other possible in vitro post-translational modifications (PTMs).

Heterogeneity in glycosylation is of in vivo origin and of great importance. Over 130 distinct glycopeptides have been seen in therapeutic antibodies of which a small number negatively impact mAb quality. Two non-human glycan epitopes, galactose-α-1,3-galactose (α-gal) and Neu5Gc-α-2-6-galactose (Neu5Gc) are antigenic when attached to monoclonal antibodies (mAbs), while α-gal alone is not. Glycosylation of a therapeutic protein is affected during manufacturing by the culture medium, changing levels of protein expression, and the physiological status of host-cells. Changes in fermentation conditions can alter site occupancy and glycan heterogeneity. This, of course, can influence the therapeutic profile of an mAb. Being able to assess glycosylation is a preferred tool in continuous process validation. How that is done will be explained later.

Structural attributes that occur exclusively in a single proteoform are of a third, less common type.

Mixing Heterogeneity in a Fermentor

Within large scale fermentors, axial flow barriers create gradients in substrate concentration, pH, and oxygen that repetitively stress cells as they pass from zones of high to low concentration. During fermentation campaigns, this causes population heterogeneity that is distributed across the population rather than following average characteristics. This population heterogeneity complicates process optimization and contributes to product quality. Mixing heterogeneity is assessed by determining substrate concentration at various sampling sites in the fermentor.

Top-Down Analysis of Proteoforms

Identification and quantification of proteoform structural attributes by the CPV system are based on the analysis of intact proteins in sector one and proteolysis fragments thereof in the BU sector 16. Chromatographic and electrophoretic separations have been widely used to separate and identify proteoforms based on their retention time. With intact monoclonal antibodies, strong and weak cation exchange chromatography has been widely used to separation charge variant proteoforms. The rationale in this approach is that charge variations such as in deamidation are most easily recognized by ion exchange chromatography. Clearly the probability of separating proteoforms depends more on the location of their chromatographic interaction site on a sorbent than their bulk properties. That is the rationale for using columns in the column array 25 with different retention mechanisms in the top-down sector 14. This increases the probability that site(s) differing in structure will be probed. The mechanism by which proteins are separated with an IMAC column is very different for example than that involved in strong cation exchange and hydrophobic interaction separations. Structural features adjacent to groups involved in adsorption are actively involved in binding to a stationary phase.

Generating a proteoform retention map through multiple modes of chromatography, such as the map shown in Table 1 below, would have the highest probability of validating the continuity of a process. The rationale in this approach is that multiple structural features are being probed. In one example, a series of subtilisin proteoforms were synthesized by single amino acid substitutions at amino acid 166 to assess this phenomenon. As seen in Table 1 below, identifications are more definitive when using proteoform retention times from multiple chromatographic modes. The elution order of subtilisin proteoforms differing by a single amino acid varies substantially with the separation mode. Although the level of specificity seen with subtilisin may not apply to all proteoform families, differentiation between proteoforms with multiple retention modes will still be superior to a single separation mode. That is the basis for use of multimodal differentiation between proteoforms in the CPV system. Depending on the degree of in vitro post-translational modification, fifty or more proteoforms could have been generated that vary a hundred-fold or more in relative concentration. Thus, the most abundant proteoforms seen in the top-down mode will be of in vivo origin.

TABLE 1

Selectivity differences between separation modes.

| Amino Acid Substitution | Elution Order | | |
|---|---|---|---|
| | SCX | IMAC | HIC |
| D166 | 1 | 2 | 1 |
| E166 | 2 | 1 | 2 |
| G (wt) | 3 | 9 | 10 |
| N166 | 4 | 4 | 4 |
| S166 | 5 | 8 | 9 |
| M166 | 6 | 3 | 12 |
| H166 | 7 | 11 | 3 |
| R166 | 8 | 7 | 6 |
| K166 | 9 | 10 | 7 |
| P166 | 10 | 5 | 5 |
| V166 | 11 | 3 | 11 |
| Y166 | 12 | 6 | 8 |

Affinity Chromatographic Purification of Analytes

The CPV system applies both top-down and bottom-up methods to confirm process continuity using a decision tree format. As explained more fully below, one limb of the chromatographic mode decision tree uses intact proteoform analysis methods outlined above. A second limb of the tree applies bottom-up analyses to further confirm that a deviation has occurred at a structural level using peptide fragments.

As proteoforms elute from columns in the top-down separation mode, they are still contaminated with host-cell proteins, metabolites, and feed stock materials. Further purification is achieved by passing effluent from a column in column array 25 in the TD sector 14, or through a sector bypass 25a, into a molecular recognition type affinity matrix. When structural features of a whole proteoform family are being examined the TD sector mcsv valve 30 is put in the bypass position to the sector bypass 25a, allowing a sample from the fermentor to pass directly into the affinity/proteolysis column. Bypassing the TD sector is preferred when analytes from a large sample volume are being concentrated on the affinity/proteolysis column of the array 27 in the BU sector 16. Samples in this case contain the entire proteoform family.

In a specific example, an mAb Fc targeting stationary phase is used to capture mAb proteoforms in a 2.1×50 mm column packed with 10 um particle size sorbent of 100 ηm pore diameter. Based on the fact that adsorbed proteoforms are digested with soluble trypsin in the affinity column, non-trypsin digestible affinity selectors are use; preferred sorbents being an immobilize peptide, affimer, or aptamer.

Bottom-Up Analyses

A complicating feature of fermentor-based post-translational modifications is the in vivo and in vitro mechanism in which they are formed (see FIG. 2). In either case it is much easier to look for PTM variants in the bottom-up mode, rather than in the top-down mode. In vivo glycosylation can produce more than a hundred glycopeptide variants upon trypsin digestion of a monoclonal antibody family. This level of difference cannot be examined with intact proteins.

As described above, an Fc targeting stationary affinity sorbents that resist trypsin digestion is used to capture mAb proteoforms. Upon completion of proteoform or proteoform family affinity selection, a volume of thermally stabilized trypsin (pH 7.8 buffer) twice that of the affinity column void volume is pumped into affinity column 60 at a flow rate of 45 uL/min. At the completion of trypsin loading, enzyme flow into the affinity column of column array 27 is terminated by switching the detector 50 back in-line with the top-down sector. This allows continued use of the top-down sector for intact protein separations while the second sector is being used for bottom-up analyses.

Proteolysis is achieved in a stopped flow mode in the affinity column 60 at a temperature of 25-50° C. Thermal stabilization of the proteolytic enzyme is further enhanced in some cases with a soluble additive such as glycerol introduced through one of the ports 43-44. At elevated temperature i) conformation of the bound proteins is altered, ii) analytes are frequently desorbed from the affinity matrix, iii) digestion time is reduced, and iv) the need for reduction and alkylation is circumvented. The resulting —S—S— bridged dipeptides also allows proteoforms disulfide bond analysis. Conformational changes un-mask digestion sites and desorb proteins from the affinity column, all of which accelerate proteolysis. Although trypsin is used in most cases, any single or a combination of proteolytic enzymes can be used to execute protein digestion in the aptamer affinity column.

Proteolysis does not have to be complete to generate proteoform specific signature peptides for quantification and glycopeptide analysis. The time required for proteolysis is proteoform specific, needing to be worked out in process development.

Following completion of proteolysis, the bottom-up gradient pump 23 was purged with 10 mM phosphate buffer (pH 7.8) and connected in series with a column of column array 27 in the BU sector 16 at a flow rate of 45 uL/min. The BU sector column can be a phenylboronate column, an ion exchange column, or a reversed phase column. At pH 7.8 the stationary phase of the phenyl boronate column is negatively charged and electrostatically adsorbed trypsin (pI~10.1-10.5) while vicinal diol bearing species were retained by formation of a boronate ester. Most non-glycosylated peptides are unretained and are adsorbed by a down-stream 2.1×30 mm reversed phase chromatography (RPC) column of the column array 26.

Upon completion of analyte transfer out of the affinity/proteolysis column the affinity and boronate columns of the array 27 are switched off-line while the RPC column is left in-line with the bottom-up sector gradient pump. The RPC column is then purged with two column volumes of aqueous mobile phase to remove non-volatile salts before switching it in-line with the mass spectrometer 40. The RPC column is gradient eluted with a mobile phase gradient ranging from aqueous 0.1% acetic (AA) or trifluoroacetic acid (TFA) to 80% aqueous acetonitrile/0.1% AA or TFA (v/v). The ideal mobile phase for each mAb was developed for each therapeutic monoclonal antibody in the process qualification stage of method development. Hydrophobic, cationic, and anionic pairing agents were used in maximizing peptide resolution, particularly in the case of detection of in vitro generated PTM-peptides. Detection was typically achieved by absorbance at 215 $\eta$m and LC-MS analyses. Quantification is generally achieved in bottom-up analyses by multiple reaction monitoring using stable isotope coding, as described below.

Upon completion of the non-glycosylated peptide RPC analysis the bottom-up sector gradient pump is connected in series with the boronate column in column array 27 and the bypass line 26a in column array 26 at a flow rate of 45 uL/min. Trypsin is eluted from the boronate column using an ionic strength gradient ranging from 10 mM to 200 mM NaCl in tris buffer (10 mM, pH 7.5). Elution is monitored with the absorbance detector at 280 $\eta$m. The rationale in this step is to remove trypsin from the glycopeptide component of the peptide mixture being analyzed.

Following trypsin elution, the boronate column of the column array 27 is connected in series with either the HILIC or RPC column of column array 26, by operation of the mcsv valves 31, 32, and purged. The HILIC column is used to probe glycosylation, whereas selectivity in the RPC column is greatest with the peptide portion of glycopeptides. Glycopeptide desorption from the boronate column requires a volatile acidic mobile phase. Boronate esters involved in glycopeptide retention on the phenyl boronate stationary phase are hydrolyzed by an acidic mobile phase and use of volatile mobile phases to allow down-stream analysis by LC-MS. When glycopeptides are being transported to a down-stream HILIC column the mobile phase is of high organic solvent content to assure capture at the inlet of the HILIC column. Transfer to an RPC column is also examined using acidic aqueous mobile phases. Glycopeptide quantification is achieved by multiple reaction monitoring as explained more fully below.

It is critical to note that the structure and retention time of peptides eluting from the HILIC and RPC columns of column array 26 is determined in process development based on LC-MS analyses of synthetic peptides. Also, the retention times of columns used in a process monitoring campaign are recalibrated on a daily basis using the same synthetic peptide internal standards.

Protein Aggregate Analysis

Under certain conditions mAb aggregates are formed during fermentation, the larger of which are immunogenic. Proteoform aggregate ($Pf_n$) concentration decreases with size, where n equals the number of proteoforms in the complex. Proteoform composition is less important than the degree of aggregation and relative amount. Detection of aggregates bearing more the four proteoforms is generally below the limits of detection. In one specific embodiment, size exclusion chromatography (SEC) columns of 4.6×300 mm packed with 3 um particles of 30 $\eta$m pore diameter are used to evaluate aggregate size.

Pre-Analysis Affinity Purification of a Proteoform Family

Recalling that all forms of a mAb are mixed with host-cell proteins, mAb aggregates eluting from the SEC column are mixed with contaminants and difficult to detect. This problem can be addressed in two ways. An affinity chromatography (AFF) column 34 in the TD sector 14 (prior to the mcsv valve 30) can be incorporated into the CPV system 10 to purify all forms of the mAb while impurities are directed through the bypass line 25a by mcsv valve 30 to waste W, HCP, or metabolite analysis. The affinity sorbent in the AFF column 34 allows desorption at near physiological pH under gentle conditions. This allows down-stream separation of proteoforms on any of the columns connected to mcsv valve 30. Since all of the substances eluting from the AFF column 34 are mAb proteoforms they are detected by absorbance at 215 $\eta$m. The second mode of detection is by continuous flow detection, as described below.

Continuous Flow Detection of Proteoforms

It is necessary in continuous process monitoring of monoclonal antibody production to: i) enable multiple proteoform identification and quantification by structure specifically distinguishing between analytes and non-analytes; ii) accomplish this task within an hour to enable recognition of process deviations; iii) repeat this analysis 300-500 times during a production run; v) digitize these analyte measurements as they are made; vi) assess quality and/or process continuity in real time; and vii) use this data to develop down-stream analysis methods.

Proteoform specific detection as described herein occurs in a series of coupled steps using molecular recognition reagents introduced through one of the ports 41-46. The first step is proteoform resolution by a chromatographic or electrophoretic means before sensing. This circumvents the proteoform discrimination problem noted above. The degree to which proteoforms are differentiated is a function of the resolving power of the separation method. Chromatographic resolution in each sector can be maximized through a combination of mobile phase gradient elution, gradient shape, mobile phase pH and ionic strength, and column temperature.

A second level of discrimination is to non-covalently tag each proteoform with a molecular recognition type, high affinity tagging agent 1 (ATA1), having unique spectral properties. The ATA1 binding site must be in a structural domain common to all proteoforms. When analytes are pre-tagged with a tightly bound fluorescent labeled tagging reagent (see FIG. 5A) the analyte:reagent complex remains intact during separation by IEC (column array 27), HIC or IMAC chromatography (column array 25) and most electrophoretic modes. It is critical that mobile phases not diminish association of the tagged proteoform complexes. As proteoform complexes eluted from the separation system, they were detected directly by their fluorescence. Issues with this method can be that the tagging agent diminishes proteoform resolution. Fluorescence can be enhanced or quenched by the analyte. Equimolar fluorescence is not obtained. Dissociating the affinity tagging agent from proteoforms before detection circumvents this problem (FIG. 5A).

Figures 5A, 5B, 5C, 5D, 5E:
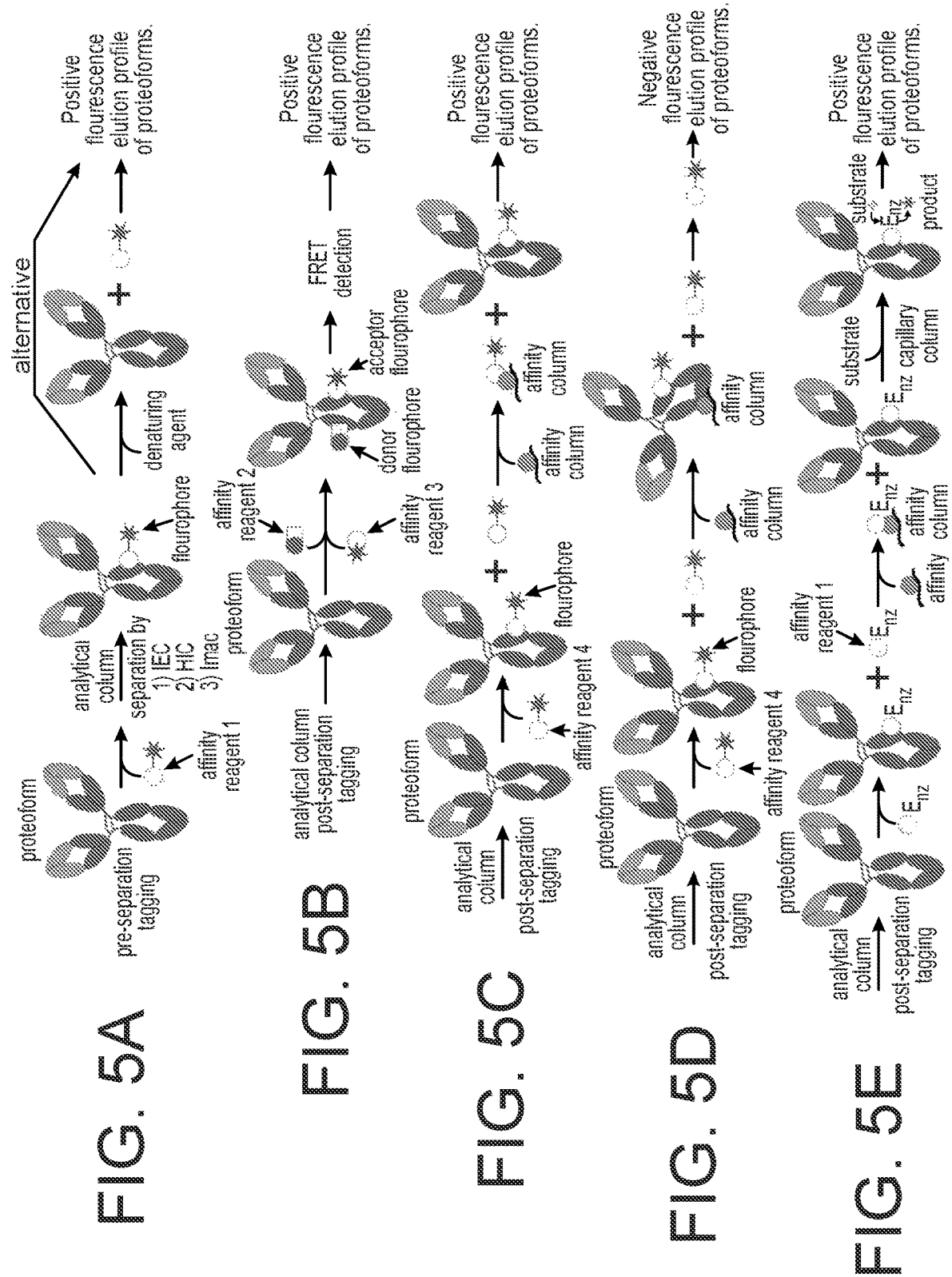
FIGS. 5A-E are diagrams showing steps in proteoform specific detection.

Förster resonance energy transfer (FRET) detection can also be used (see FIG. 5B). In addition to labeling proteoforms with a ATA1 in the Fc domain, a second high specificity tagging agent (ATA2) is continuously added to the chromatographic or electrophoretic column effluent. Because the ATA1 and ATA2 binding sites are both in the Fc domain, they are sufficiently close to allow fluorescence energy transfer between the ATA1 donor species to the ATA2 acceptor, enabling FRET. Peptides, affimer, or aptamers are the preferred molecular recognition reagents. The donor-to-acceptor separation distance $\underline{r}$ should typically be no more than 10 ηm. The relationship between Förster resonance energy (E) transfer and the distance $\underline{r}$ is seen in the equation $$E = \frac{1}{1 + (r/R_0)^6}.$$

The Förster distance constant $R_0$ is a function of the i) overlap of the donor emission and acceptor absorption spectra and ii) the distance at which the energy transfer efficiency for a particular donor-to-acceptor pair is 50%. The fact that FRET energy (E) is inversely related to the sixth power of the distance ($\underline{r}$) between the donor and the acceptor tags means the tag binding sites must be relatively close. This is the reason for using small molecular recognition affinity reagents in ATA1 and ATA2 that bind in the Fc region of mAbs. The great advantage in this approach is in eliminating solid phase adsorption along with solid phase sorbent recycling.

Other post-separation tagging methods requiring a solid phase extraction component are seen in FIG. 5C-5E. The method illustrated in FIG. 5C entails the use of an excess of fluorescent labeled affinity tagging reagent that binds with high specifically and affinity to all proteoforms as they eluted from the separation system. The solution is then passed through an affinity chromatography column that subtracts the tagging reagent. The affinity column is recycled periodically. A limitation of this approach is that the relative molar response of all proteoforms is identical.

The method illustrated in FIG. 5D is the reverse of that in FIG. 5C. In this approach the fluorescent tagged proteoform is extracted with an affinity column and the residual fluorescent labeled tagging agent is detected. An advantage of the method of FIG. 5D over the method of FIG. 5C is that it circumvents the relative molar response issue. Another feature of this approach is that the elution profile shows negative peaks. Proteoform concentration is seen as negative peaks in the elution profile.

The method illustrated in FIG. 5E uses enzyme amplification in proteoform detection. A high turnover enzyme conjugated antibody tagging reagent is continuously added to the effluent from the separation system to enable non-covalent enzyme tagging of proteoforms. Subsequent to proteoform:enzyme complex formation excess tagging agent is removed by passage through a solid phase affinity sorbent. Following passage through the affinity sorbent substrate is added to the proteoform:enzyme complex and passed through an open-tubular capillary before product detection. A limitation of this approach is the additional time required for product formation.

Isotope Coding and Labeling

Figure 7:
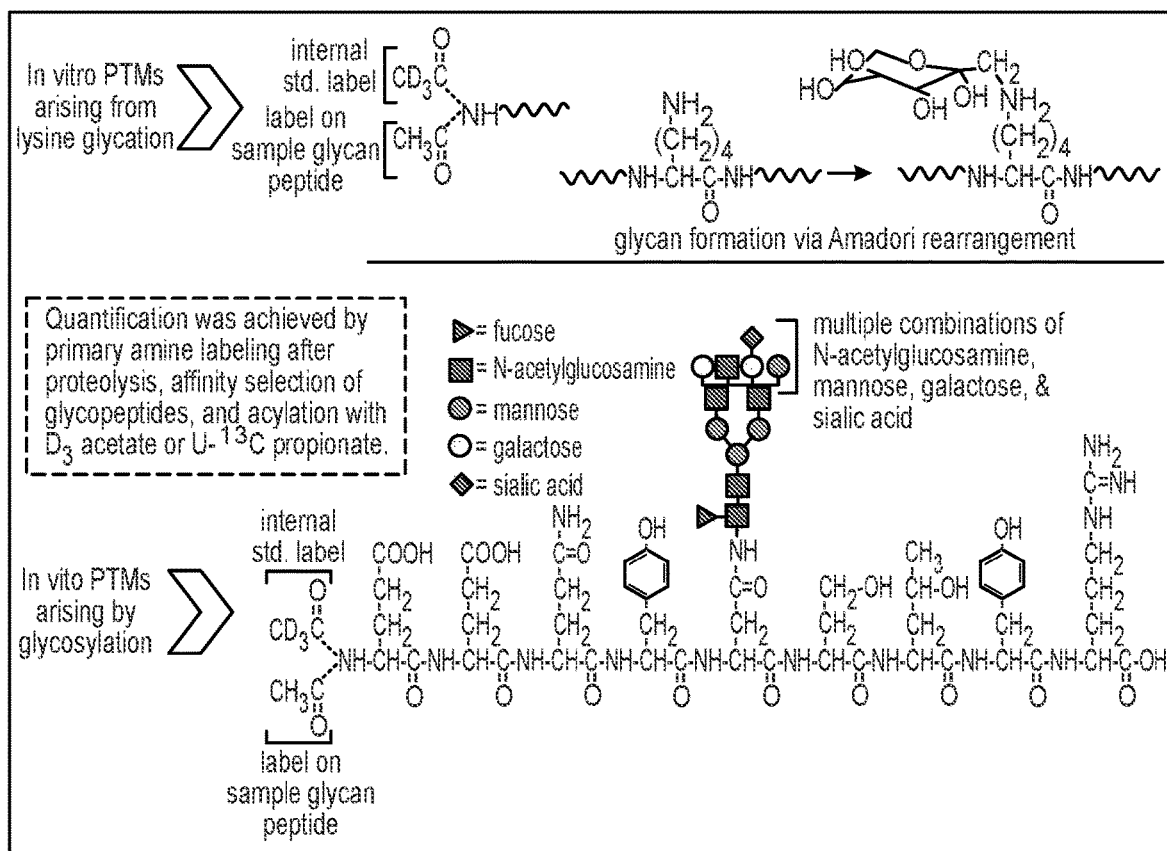
FIG. 7 is a diagram showing steps in glycated and glycosylated peptide derivatization.

Quantification at the bottom-up peptide level is generally achieved by multiple reaction monitoring (MRM) with heavy isotope labeled standards as illustrated in FIGS. 6-7. The methods involved are based on the addition of known quantities of heavy standards to samples followed by MS based isotope analysis to determine the ratio of labeled to unlabeled peptides in samples. As noted above, a monoclonal antibody is actually a family of more than a hundred structurally related proteoforms. Beyond approximately 5 isoforms that arise from variations in splicing, enzymatic editing, and reading frame shifts at the gene processing level the bulk of proteoforms emanate from in vivo and in vitro post-translational modifications (see FIG. 2). In vivo PTMs are by far more frequent; coming from variations in the N-glycome linked to the EEQYNSTYR tryptic peptide in the Fc region of proteoforms. A much smaller number of PTMs were generated in vitro.

Among the common in vitro post-translational modifications (PTMs) pyroglutamate formation at N-termini, degradation at N- and C-termini, sulfhydryl and disulfide bridge scrambling, deamidation, methionine oxidation, tryptophan oxidation, histidine oxidation, and glycation via an Amidori rearrangement (FIG. 6) are the most common. The sequence and location of PTMs in peptides is determined LC-MS in discovery/development stage of process development. Following trypsin digestion of proteoforms, peptides bearing these PTMs generally reside in signature peptide sequences of fewer than 10 amino acids with a lysine or arginine at their C-termini. Heavy isotope coding is achieved with these peptides by de novo synthesis through incorporation of $^{13}C$ and $^{15}N$ labeled amino acids at specific positions in the sequence. Amino acids used in coding are seen in Table 2 below. With uniform labeled lysine or arginine (U-$^{13}C_6$, $^{15}N$) the mass difference between labeled peptides and those from the sample was 8 or 10 Dalton (Da) respectively. Labeled signature peptides at least three atomic mass units heavier than sample peptides were used to preclude overlap of isotope peaks.

TABLE 2

Labeled Amino Acids Used In The Synthesis of Signature Peptides

| Amino Acid | | Labeling Position | Mass Shift. |
|---|---|---|---|
| Alanine | A | 2-$^{13}$C, $^{15}$N, | 2 Da |
| Asparagine | N | $^{15}$N$_2$, | 2 Da |
| Alanine | A | U-$^{13}$C$_3$, | 3 Da |
| Alanine | A | U-$^{13}$C$_3$, $^{15}$N | 4 Da |
| Proline | P | U-$^{13}$C$_5$, $^{15}$N | 6 Da |
| Valine | V | U-$^{13}$C$_5$, $^{15}$N | 6 Da |
| Asparagine | N | $^{13}$C$_4$, $^{15}$N$_2$, | 6 Da |
| Asparagine | N | $^{13}$C$_4$, $^{15}$N$_2$, | 6 Da |
| Isoleucine | I | U-$^{13}$C$_6$, $^{15}$N | 7 Da |
| Leucine | L | U-$^{13}$C$_6$, $^{15}$N | 8 Da |
| Lysine | K | U-$^{13}$C$_6$, $^{15}$N | 8 Da |
| Arginine | R | U-$^{13}$C$_6$, $^{15}$N | 10 Da |
| Phenylalanine | F | U-$^{13}$C$_9$, | 10 Da |

Coding by Derivatization

FIG. 7 shows the manner in which in vitro glycated peptides and in vivo glycosylated peptides differ in origin and structure from the PTM peptides seen in FIG. 6. In view of the complexity of glycated and glycosylated peptides, de novo synthesis would be difficult and costly. Moreover, trypsin digestion produces at least one primary amine on a glycated or glycosylated peptide; allowing amine acylation. Using N-hydroxysuccinimidyl-$^2$H$_3$-acetate internal standard peptides are prepared that are 3 Daltons heavier that acetylated sample peptides. A small number of glycated peptides bearing a C-terminal lysine are an exception. Internal standard and sample peptide differed by 6 Daltons in this case.

Preanalytics Servicing

It will be appreciated by one skilled in the art that all consumables in a process monitoring system must be replaced before each production run and the system recalibrated with analyte standards. The signature peptides standards and intact proteoform samples serve as a retention time training set for proteoforms and signature peptides encountered by the new columns and mobile phases pending use in a production campaign.

The Software Component

As outlined in the flowchart of FIG. 1, the function of CPV system software implemented within controller 20 is to: i) rapidly gather chronological data on multiple biological and environmental variables during production that impact therapeutic protein quality; ii) assess process continuity based on hourly sampling across a production run; iii) tentatively identify proteoform variants based on top down data; iv) develop analytical protocols to confirm variant identities based on artificial intelligence; v) compare the results to reference manufacturing campaigns; and vi) implement a decision. The term variable as used in data analysis defined as a specific environmental, structural, or constituent ratio feature that if altered could modify therapeutic efficacy. Measurements of structural variables that impact efficacy and critical quality attributes (CQAs) are referred to as direct quality measurements. Known cases of direct variables are: i) the rate at which mAb proteoforms are synthesized; ii) proteoform ratio changes during production arising from cellular expansion, aging, and death; and iii) changes in therapeutic efficacy (biological activity) evolving from variations in proteoform ratios. Assessment of environmental variables such as temperature and pH that could alter quality and are designated indirect measurements in that they do not directly monitor quality.

Data acquisition and analysis can be handled with five types of software tools implemented by the controller 20. Type 1 (system calibration) software assures i) the analytical platform is properly configured to operate unattended throughout a production run by ii) continuously monitoring mobile phase and reagent consumption. Step one in the pre-analysis check list is user specification of all the analytical methods that artificial intelligence selects and uses in sample analysis during the production campaign, including the probable number of samples that would be analyzed. Methods can be locked in by stipulating "repeat settings from the last production run." Construction of these methods made with Type II analytical management software, as described below. With this information the system determines the requisite consumables and whether they are loaded in the system via a bar code reader (not shown). Use of the columns in the column arrays 25-27 is recorded during production, compared to the column half-life, and become part of the analytical output for each analysis. A system alarm is triggered if column use exceeded the recommended half-life. Volumes of mobile phases ($P_m$) and reagents are monitored by mass and reported by percent residual volume, again being recorded with sample analysis data. An alarm is triggered when 75% of a $P_m$ or reagent has been used. The platform also monitors check valve leakage and pumping accuracy but only reports this data when a problem is detected.

Type II (analytical management) software can be of two types. One is designed to store and execute individual methods upon request. Required columns, pump selection, mobile phase selection, gradient programming, mode of detection, and a column recycling protocol were stored for each method. Thirty to 50 methods could be constructed and stored during process development. All of these methods can be uploaded from an R&D center to the CPV system 10 controller 20. The mass spectrometer (MS) 40 can use a separate data system for storing methods, with individual methods stored in the same way. In a final step of platform preparation, the data system determines that the correct columns of arrays 25-27, mobile phases and reagents are loaded and sufficient for the process campaign. Reagents can be introduced into the column arrays 25-27 through respective inlets 41-46.

Many analyses require the use of multiple analytical methods operating independently in different sectors 14 and 16 or sequentially in a single sector 14 or 16. This is addressed with a second type of analytical management software that assembles individual methods into an integrated analytical protocol. Again, the order in which various methods are executed in analyzing a sample can be determined in process development and integrated into the Type II software of the controller 20. This set of methods is recalled and integrated by a specific execution name. At a higher level a series of these integrated protocols are sequentially implemented by software that allows other pieces of software to communicate.

Type III (data acquisition) software is used to acquire data from a fluorescence detector (FD) 50, an absorbance detector and mass spectrometer 40, and all the environmental sensors 55 for each sample. Although the environmental sensors 55 generate data continuously, only data at the sampling start time is recorded. Chromatography or electrophoresis data is plotted in a two-dimensional format wherein elution time forms the X axis and signal intensity the Y axis. Each peak is quantified and identified based on the retention time of standards in the retention time training set and an algorithm that compensates for retention time drift for each column during a production run. Environmental sensor data is recorded as a single intensity value for each of the sensors 55. The entire set of analytical data from each sample is integrated, numbered in chronological order, and time stamped.

Type IV (data analysis) software is of two types—one used in top-down analysis of intact proteoforms and the other in bottom-up analysis employed in signature peptide identification and quantification. The primary function of the top-down software is to identify process changes at the proteoform level using retention time-based identification, determination of concentration ratios, and identification of changes in their rate of synthesis. This is achieved by multivariate statistical analyses on acquired chromatographic or electrophoretic data. Process validation is presented in the form of confidence intervals, charts depicting acceptance ranges, and distribution plots of intra- and inter-batch variables. $T^2$ control charts can be used to detect shifts in the process.

In contrast, bottom-up analyses is directed to identifying biological variables in the fermentation system that changed during production. This systems biology is defined as the computational-based mathematical analysis and modeling of complex biological phenomena, as illustrated in the chart of FIG. 2. These biological variables are described above in the section "Compartmentation of proteoform synthesis." It is fortuitous that many of these changes are easily identified in proteoform families through signature peptides. Based on the use of $^{13}C$-labeled internal standard signature peptides in the MRM method of peptide quantification these methods are very accurate. The same multivariate statistical analysis methods are used as described above but with the goal of understanding continuous process validation more fully at the systems biology level.

These two methods of data analysis provide different, but simultaneous methods of validating the nature of process deviations. Type IV software informs the manufacturer in real time the degree to which the manufacturing process is meeting reproducibility standards. This in turn allows feedback control. Based on the monitored elution profile information of proteoforms obtained from the absorbance and fluorescence detector 50, and the mass spectrometer 40—namely, the concentration, retention time, peak intensity, and peak area—relative ratios of peak intensity or relative ratios of peak area of the desired samples are obtained. To flag possible outlier or significant change of the desired sample, various statistical methods are being used. The standard deviation, the median value, the first and second derivative, the percent coefficient of variation (CV %), analysis of variance (ANOVA), the median absolute deviation from the median (MAD) and interquartile range (IQR) are calculated by the controller 20 and used by the controller Type IV software to validate and quantify the process. The significant variation of individual peak change is determined according to physical and biological process, or by the relative ratio of individual proteoforms.

Type V (provenance coding) software executed by the controller 20 maintains the history of everything done during a manufacturing campaign; including sources of data, archiving the nature and sources of raw materials, raw material analytical data, saving all data acquired by the system, all computations made by the system, the algorithms used to provide multivariate statistical analyses of process deviations, tracking the exchange of data between computers, carry new data to definitions of acceptable product quality, comparing quality standards against acquired data, providing tamper-proof results, and generating reports automatically that serve as the basis for communication with regulatory agencies.

The controller 20 is a processor or computer adapted to execute the software described above. The controller 20 can interface with a user interface 20a that is configured to allow data entry, uploading of data to the controller software, output of data and display of information generated by the software, as described above.

The present disclosure should be considered as illustrative and not restrictive in character. It is understood that only certain embodiments have been presented and that all changes, modifications and further applications that come within the spirit of the disclosure are desired to be protected.

Definition of Terms

Absorbance detector=a device used in liquid chromatography for detecting and quantifying analyte absorbance during passage through an illuminated flow cell.

Acceptor fluorophore=a fluorescent molecular species of a fluorescence resonance energy transfer (FRET) pair that accepts light from an adjacent donor fluorophore.

Affinity chromatography selector=a molecular species immobilized on the surface of a chromatography support that structure specifically associates with high affinity and retains an analyte by molecular recognition as impurities are eluted.

Affinity columns=a packed bed chromatography column bearing an affinity chromatography selector.

Affinity targeting agent (ATA)=a soluble molecular species that structure specifically associates with a complimentary structural domain.

Alexa Fluor 546/Alexa Fluor 594=a fluorescence resonance energy transfer (FRET) pair of which Alexa Fluor 546 is the donor fluorophore and Alexa Fluor 594 is the acceptor fluorophore.

Aminophenyl boronate column (ABC)=when immobilized on a solid phase chromatography support ABC captures molecular species bearing a vicinal diol from samples eluted through the column.

Cation exchange chromatography=proteins and peptides with a net positive charge are adsorbed at low ionic strength to chromatographic stationary phases that are negatively charged and can be by increasing the mobile phase ionic strength or increasing the pH.

Critical Quality Attribute=a chemical property that should be within an appropriate limit, range, or distribution to ensure the desired product quality.

Donor fluorophore=a fluorescent molecular species used in fluorescence resonance energy transfer (FRET) that donates light from an adjacent acceptor fluorophore.

Endo-metabolites=metabolites contained within a cell.

Exo-metabolites=metabolites in the growth medium surrounding cells in a fermentor.

Glycation=the process by which a sugar binds in vitro to a protein through an Amadori rearrangement.

Glycan=an oligosaccharide

Glycated protein=a protein to which a monosaccharide is linked by Schiff based formation with an Amadori rearrangement.

Glycome=the entirety of glycans coupled to proteins.

Glycopeptide=is a peptide of interest in the case of an mAb having an oligosaccharide bound to a residue.

Glycosylated protein=a protein to which glycans are coupled via a biosynthetic pathway.

Hydrophilic interaction chromatography=separates molecules on the basis of their hydrophilicity. It is a type of separation in which a polar molecule in an organic mobile phase adsorbs on a polar stationary phase and is caused to elute by increasing the aqueous content of the mobile phase.

Hydrophobic interaction chromatography=a type of chromatography wherein the stationary phase is a weakly hydrophobic species. Interaction of the protein analyte to the stationary phase is promoted by a high concentration of a high surface tension inducing salt such as ammonium or sodium sulfate and lowering the salt concentration causes elution.

Immobilized metal affinity chromatography=A type of chromatography in which proteins and peptides bearing histidine and cysteine with high affinity for chelated metals can be separated in the pH range from 6-8.

Lectin affinity chromatography=a type of affinity chromatography in which the stationary phase is a protein (lectin) with an affinity for a particular type of glycan.

Molecular reaction monitoring=the addition of a known concentration of a heavy isotope labeled version of a substance to a sample as an internal standard that when analyzed by mass spectrometer enable relative concentration measurements to be made based on isotope ratio analysis.

Molecular recognition=a specific interaction between two or more molecules, which exhibit molecular complementarity, based on non-covalent bonding such as hydrogen bonding, metal coordination, hydrophobic forces, van der Waals forces, $\pi$-$\pi$ interactions, and/or electrostatic effects.

Non-glycosylated peptide=peptide that does not bear a covalently associated glycan.

Proteoform family=a group of protein with substantially similar structural domains.

Proteoform=a member of a proteoform family.

Genetically engineered cells=cells that have been genetically modified to produce protein(s) of a particular amino acid sequence.

Process validation=assessing the degree to which a manufacturing process is reproducible.

Recombinant proteins=proteins expressed by genetically engineered cells.

Reversed phase chromatography=a type of chromatography in which the stationary phase is a covalently immobilized hydrocarbon.

Signature peptide=a peptide fragment derived from either a single proteoform or multiple members of a proteoform family having an amino acid sequence that is either i) unique to one or more family members or ii) bears a particular type of post-translational modifications.

Size exclusion chromatography=a form of liquid chromatography that separates molecular species based on their hydrodynamic volume.

Trypsin=a proteolytic enzyme that hydrolyzes amide bond cleavage between the carboxyl group of an arginine or lysine and another amino acid.

What is claimed is:

1. An integrated analytical process for chronologically assessing the concentration of proteoforms in a family of protein variants contained within complex biological compositions obtained from a fermentor that is part of a manufacturing process for the production of the complex biological compositions, the compositions derived from an expanding native or genetically engineered cell culture of microbial, plant, animal, or human origin, the process comprising the steps of:

a) providing at least a two-sector separation system including;
   a top-down (TD) sector including a plurality of distinct TD analysis columns that are configured and operable for intact proteoform resolution, detection of specific analyte proteoforms in samples bearing host-cell proteins, proteoforms, and metabolites, identifying and quantifying these components for the purpose of chronologically validating manufacturing process reproducibility;
   a bottom-up (BU) sector including a plurality of distinct BU analysis columns configured and operable for affinity purification and proteolysis of proteoforms during transport into the BU sector; and
   a controller configured and operable to select and assemble analytical protocols that will identify signature peptides while the two sectors are operating independently, either in tandem or parallel;
(b) choosing conditions, sampling times, analytical method steps, and a system configuration for the TD sector to automate the generation of analytical data to validate a manufacturing process incorporating the fermentor, wherein data from individual analytical steps is chronologically converted by the controller into digital data blocks that provide a means to evaluate i) analyte variation during a production run relative to earlier time points within the process and equivalent chronological steps in prior production runs, ii) the presence of proteoforms bearing positive and negative structural attributes that impact human health, iii) the need for short term and long term remediation of process deviations, and iv) process continuity relative to prior production runs,
(c) obtaining analytical samples of the complex biological composition from the fermentor at designated times and removing particulate matter prior to delivery of the analytical sample to one of the sectors;
(d) maximizing proteoform resolution of a specific monoclonal antibody proteoform family in multiple chromatographic or electrophoretic separation modes of differing selectivity, within one or more of the TD and BU analysis columns, to identify and quantify proteoforms by separation methods alone;
(e) detecting individual members of an analyte family in the presence of host-cell proteins as they elute from analysis columns in the TD sector;
(f) sequentially accumulating and time stamping analyte detection data from samples within a proteoform family passing through the TD sector, and acquiring contemporaneous data from sensors detecting the environment of the fermentor, instrument performance data, and run-time data, and then constructing time-versus-analog response curves that are digitized and saved as digital data by the controller,
(g) comparing current data with data from earlier sample times and samples and chronologically equivalent data from prior production runs; whereupon qualitative and quantitative similarities between the current and earlier data is used by the controller to assess one or more potential deviations in the manufacturing process;
(h) confirming the one or more potential deviations in the BU sector using either a proteoform derived from the TD sector or an unfractionated proteoform family that has been affinity selected, reduced or digested with a Pep-Fc-proteolysis column before analysis of the resulting peptide classes in the BU sector, wherein the affinity column is resistant to trypsin digestion;

(i) providing individual analyses of the peptide classes by one of multiple selective modes of liquid chromatography designated by the controller in combination with mass spectrometry, wherein the liquid chromatography modes can be by phenylboronate, reversed phase, hydrophilic interaction, or molecular recognition-based affinity chromatography;

(j) providing absorbance and/or mass spectral detection and analysis of the separated signature peptides in the BU sector;

(k) providing quantification of the peptides through multiple reaction monitoring by mass spectrometry;

(l) chronologically converting analytical data from one or more detectors in the BU sector into digital data that can be evaluated by the controller to assess and confirm i) variations during a production run relative to earlier time points within the process and equivalent chronological steps in prior production runs, ii) the presence of signature proteoforms bearing positive and negative structural attributes that impact human health, iii) the need for short term and long term remediation of process deviations, and iv) process continuity relative to prior production runs, and (m) constructing a digital provenance of the manufacturing record at the end the production run based on the chronological analytic data that can be evaluated by a federal regulatory agency and that can be subsequently used to improve the process.

2. The method of claim 1, wherein in step (a) each of the at least two sectors includes a switching valve that is controllable by the controller to select among the plurality of analysis columns in the corresponding sector for specific fraction selection from any column in the TD sector for transport into the BU sector, for molecular affinity selection and proteolysis between the TD and the BU sectors, and for transport of peptides into the BU sector for resolution and separation of peptides in multiple separation modes.

3. The method of claim 2, wherein the controller operates the switching valve for the TD sector so that samples drawn from the fermentor bypass the plurality of TD analysis columns, and operates a sector coupling valve to connect the bypass of the TD sector to a proteoform affinity column in the plurality of BU analysis columns for subsequent proteolysis and bottom-up peptide analysis in the BU sector.

4. The method of claim 2, wherein samples from the fermentor are shunted by operation of the controller through a TD sector bypass to an affinity column at the sector coupling valve where a proteoform family is purified and subsequently analyzed in the bottom-up mode in sector two without proteolysis.

5. The method of claim 2, wherein the controller provides a sample to each of the TD and BU sectors to simultaneously perform top-down proteoform analyses.

6. The method of claim 2, wherein at least two different types of liquid chromatography can be selected for proteoform analysis in either a top-down or a bottom-up mode of analysis in the TD and BU sectors.

7. The method of claim 6, wherein the types of liquid chromatography include one or more of ion exchange (IEC), reversed phase (RPC), hydrophobic interaction (HIC), hydrophilic interaction (HILIC), immobilized metal affinity (IMAC), molecular recognition affinity, size exclusion (SEC), lectin affinity chromatography.

8. The method of claim 2, wherein an affinity chromatography column that allows both proteoform purification and proteolysis of native or reduced analytes is used to connect the TD and BU sectors.

9. The method of claim 8, wherein reduction and proteolysis are used to dissociate and fragment heavy and light chains of the analyte captured by the affinity column, the chains being Fab, Fab', F(ab')2, or Fv fragments of an antibody, wherein the reduction and proteolysis is accomplished by one or more of chaotropic agent, nonionic detergent, reducing agent, alkylating agent, and enzymes introduced either as a soluble reagent or immobilized on nanoparticle.

10. The method of claim 2, wherein the BU analysis columns include columns selected for one or more of ion exchange (IEC), immobilized metal affinity (IMAC), hydrophilic interaction (HILIC), phenylboronate, reversed phase (RPC), molecular recognition-based affinity, and size exclusion chromatography (SEC).

11. The method of claim 1, wherein in step (a), the TD and BU sectors each include a capillary electrophoresis or electrochromatography channel, and the method further comprises achieving proteolysis in a reactor connected to a separation channel to which a non-trypsin digestible analyte affinity selector is immobilized, selected analytes are subjected to proteolytic digestion therein, and peptides are resolved in the BU sector by capillary electrophoresis or electrochromatography with suitable enzyme addition.

12. The method of claim 11, wherein the electrophoretic separation modes are selected from one or more of capillary zone electrophoresis, capillary isoelectric focusing, and capillary gel electrophoresis.

13. The method of claim 1, wherein in steps (b) and (g) proteoform ratios, changes in the rate of proteoform synthesis, and changes in signature peptide ratios are evaluated by the controller to determine process deviations.

14. The method of claim 1, wherein in step (c) an analytical sample is obtained from culture medium in the fermentor by acoustophoresis or membrane permeation to remove particulate matter and transport permeate to the TD and/or BU sectors.

15. The method of claim 1, wherein in step (c) an analytic sample is obtained by aseptic withdrawal of fermentor broth and centrifugal removal of particulates.

16. The method of claim 1, wherein in step (d) chromatographic resolution in each sector is maximized through a combination of mobile phase gradient elution, gradient shape, mobile phase pH and ionic strength, and column temperature.

17. The method of claim 1, wherein in step (d) proteoform identification is achieved through sequential application of two or more separation modes differing in proteoform selectivity during process monitoring in the TD sector.

18. The method of claim 1, wherein in step (e) fractionation of a proteoform family occurs in the TD sector, the BU sector is by-passed, and intact proteoforms are analyzed by top-down mass spectrometry.

19. The method of claim 1, wherein in step (e) analytes eluting from a TD analysis column are non-covalently derivatized with one or more molecular recognition-type affinity targeting agents (ATAs) bearing a moiety that subsequently facilitates analyte detection by absorbance, fluorescence, or Förster resonance energy transfer.

20. The method of claim 19, wherein the moiety covalently attached to the molecular recognition reagent is a fluorophore.

21. The method of claim 19, wherein a donor fluorophore is covalently linked to a first affinity targeting reagent ($ATA_1$) that structure specifically binds to all proteoforms in a structure related family and an acceptor fluorophore covalently coupled to a second affinity targeting reagent ($ATA_2$)

that binds to the analyte proteoforms at a second site, the pair being continuously added to effluent from a separation column for detection by Förster resonance energy transfer.

22. The method of claim 21, wherein the donor-acceptor pairs include one or more of fluorescein isothiocyanate/tetramethyl rhodamine isothiocyanate, Texas Red/Cy5, or Alexa Fluor 546/Alexa Fluor 594.

23. The method of claim 21, wherein both the donor and quencher fluorophore are linked to a single affinity tagging agent.

24. The method of claim 21, wherein a buffered solution of the requisite donor-acceptor pair is continuously added to the effluent from a chromatography or electrophoresis column, blended as they are transported through a short mixing column, and subsequently detected by Förster resonance energy transfer.

25. The method of claim 19, wherein the moiety on the molecular recognition affinity targeting agent (ATA) is a high turnover enzyme ($E_{pm}$) that is continuously added to a column effluent stream where it binds non-covalently to all proteoforms, the ATA~$E_{pm}$ and mAb:ATA~$E_{pm}$ complex are transported through an affinity column where unbound ATA~$E_{pm}$ is removed, substrate is added to the stream and transported through a capillary reactor and product from the mAb:ATA~$E_{pm}$ complex is detected by absorbance or fluorescence.

26. The method of claim 1, wherein in step (e) the TD sector one is bypassed and a sample is transported to an affinity column to purify a proteoform family for subsequent bottom-up analysis or direct analysis by top-down mass spectrometry.

27. The method of claim 26, wherein glycopeptides produced by proteolysis are affinity selected and then subjected to further chromatographic or electrophoretic analysis.

28. The method of claim 26, wherein non-glycosylated peptides are resolved from glycopeptides by affinity chromatography and subjected to further analysis liquid chromatography-mass spectrometry.

29. The method of claim 28, wherein quantification of signature peptides from affinity proteoforms is achieved by multiple reaction monitoring using heavy isotope labeled internal standards.

30. The method of claim 1, wherein in step (h) one or more proteolytic enzymes used in peptide formation are thermally stabilized by covalent modification.

31. The method of claim 1, wherein in step (h) the immobilized affinity selector is a polypeptide.

32. The method of claim 1, wherein in step (h) the affinity chromatography selector is resistant to proteolysis.

33. The method of claim 1, wherein in step (h) the immobilized affinity chromatography selector is selected from an aptamer, an affimer, a peptide, or a small molecule.

34. The method of claim 33, wherein the small molecule is selected from boronate and a chelation sorbent.

35. The method of claim 1, wherein in step (i) changes in the glycan structures of glycopeptides are examined in a multistep method comprising the steps of:
  selecting a proteoform for glycopeptide structure analysis by Fc region targeting affinity chromatography;
  digesting the proteoform with trypsin;
  removing non-glycosylated peptides by pumping the trypsin digest through an aminophenyl boronate column;
  desorption of trypsin from the aminophenyl boronate column with an ionic strength gradient at neutral pH;
  releasing glycopeptides from an aminophenyl boronate column by elution with sorbitol of by using an acidic mobile phase; and
  separating the desorbed glycopeptides on a HILIC or reversed phase column, and the glycopeptides are analyzed by mass spectrometry.

36. The method of claim 1, wherein in step (k) changes in the concentration, rate of synthesis, and concentration ratios of proteoforms and peptides within a production run of the manufacturing process are identified by multivariate statistical analysis and quantified using fermentor sensor, chromatographic or electrophoretic, and mass spectral data.

37. The method of claim 1, wherein changes in the relative amount or rate of synthesis of proteoforms or signature peptides associated with negative structural attributes are identified.

38. The method of claim 1, wherein a digital provenance of the most current production run of the manufacturing process is created, stored, and compared to prior production runs for the purpose of understanding production failures, improving a manufacturing process, and communicating with federal regulatory agencies.

39. The method of claim 1, wherein in step (e) changes in oxidative stress during a production run of the manufacturing process are recognized by affinity chromatographically selecting a proteoform family and quantifying comparing oxidized protein concentration from a current production run to the concentration found in previous production runs.

40. A continuous process validation (CPV) system for chronologically assessing the concentration of proteoforms in a family of protein variants contained within complex biological compositions obtained from a fermentor that is part of a manufacturing process for the production of the complex biological compositions, the CPV system comprising:
  a sampling system associated with the fermentor and operable to extract a sample of the biological composition from the fermentor;
  a top-down (TD) sector including a plurality of distinct TD analysis columns that are configured and operable for intact proteoform resolution, detection of specific analyte proteoforms in samples bearing components including host-cell proteins, proteoforms, and metabolites, and for generating data that identifies and quantifies these components;
  a TD multi-channel selection (mcsv) valve disposed between the sampling system and the plurality of TD analysis columns, the TD mcsv valve operable to direct the sample to one or more of the columns of the plurality of TD analysis columns;
  a bottom-up (BU) sector including a plurality of distinct BU analysis columns configured and operable for affinity purification and proteolysis of proteoforms during transport into the BU sector and for generating data related thereto;
  a sector coupling valve configured to selectively connect the TD sector to the BU sector for passage of the sample from the TD sector to the BU sector;
  a BU multi-channel selection (mcsv) valve disposed between the sector coupling valve and the plurality of BU analysis columns, the BU mcsv valve operable to direct the sample to one or more of the columns of the plurality of BU analysis columns; and
  a controller configured and operable to selectively actuate the sampling system, the TD mcsv valve, the sector coupling valve and the BU mcsv valve to control the flow of the sample among the plurality of TD analysis columns and the plurality of BU analysis columns according to a protocol adapted to validate the manufacturing process for the production of the complex biological compositions, the controller further configured to receive and evaluate the data from the TD and the BU sectors according to the protocol, wherein the controller is configured to determine from the data from the TD sector whether a deviation in the manufacturing process has occurred, and to direct the sample from the TD sector to the BU sector for confirmation of the deviation by the BU sector.

41. The CPV system of claim 40, wherein the plurality of TD analysis columns is selected from affinity, IMAC (immobilized metal affinity chromatography), HIC (hydrophobic interaction chromatography), HILIC (hydrophilic interaction chromatography), WAX (weak anion exchange) and WCX (weak cation exchange) and SEC (size exclusion) columns.

42. The CPV system of claim 41, wherein the TD sector includes a bypass independent of the plurality of TD analysis columns and selectable by the TD mcsv valve.

43. The CPV system of claim 40, wherein the plurality of BU analysis columns is selected from SAX (strong anion exchange) and SCX (strong cation exchange), HILIC (hydrophilic interaction chromatography), RPC (reversed-phase chromatography), WAX (weak anion exchange and SEC (size exclusion), Boronate affinity and IEC (ion exchange) columns.

44. The CPV system of claim 43, wherein the BU sector includes a bypass independent of the plurality of BU analysis columns and selectable by the BU mcsv valve.

45. The CPV system of claim 40, further comprising a PCR (post column reactor) column separate from the plurality of TD and BU analysis columns, the PCR column selectively connected to the TD sector by operation of the sector coupling valve by the controller.

46. The CPV system of claim 40, wherein each of the TD sector and the BU sector includes a corresponding pump for pumping the sample through the corresponding sector.

47. The CPV system of claim 40, further comprising a plurality of sensors for sensing the environment of the fermentor, data from the sensors provided to the controller for use by the controller in selectively actuating the sampling system, the TD mcsv valve, the sector coupling valve and the BU mcsv valve to control the flow of the sample among the plurality of TD analysis columns and the plurality of BU analysis columns according to the protocol and to evaluate the data from the TD and the BU sectors according to the protocol.

* * * * *